United States Patent
Solomon et al.

(10) Patent No.: US 6,703,015 B1
(45) Date of Patent: Mar. 9, 2004

(54) FILAMENTOUS BACTERIOPHAGE DISPLAYING AN β-AMYLOID EPITOPE

(75) Inventors: Beka Solomon, Herzlia Pituach (IL); Dan Frenkel, Rehovot (IL)

(73) Assignee: Ramot at Tel-Aviv University Ltd., Tel Aviv (IL)

(*) Notice: Subject to any disclaimer, the term of this patent is extended or adjusted under 35 U.S.C. 154(b) by 0 days.

(21) Appl. No.: 09/473,653

(22) Filed: Dec. 29, 1999

Related U.S. Application Data

(60) Provisional application No. 60/152,417, filed on Sep. 3, 1999.

(51) Int. Cl.$^7$ .......................... A01K 63/00; A61K 48/00; C12N 15/00
(52) U.S. Cl. .................................... 424/93.2; 435/320.1
(58) Field of Search .......................... 514/44; 424/93.2; 435/320.1, 455

(56) References Cited

U.S. PATENT DOCUMENTS

| | | | |
|---|---|---|---|
| 5,688,651 A | 11/1997 | Solomon | 435/7.1 |
| 5,811,093 A | * 9/1998 | Merril et al. | 424/93.6 |

FOREIGN PATENT DOCUMENTS

| | | | |
|---|---|---|---|
| EP | 0 526 511 B1 | 3/1991 | A61K/38/00 |
| WO | WO 92/07077 | 4/1992 | |
| WO | 99/27944 | 10/1999 | A61K/38/00 |

OTHER PUBLICATIONS

Verma et al (1997) Nature 389, 239–242.*
Scott et al (1990) Science 249, 386–390.*
Motti et al (1994) Gene 146, 191–198.*
Eck et al in Goodman & Gilman's the Phamacological Basis of Therapeutics, 9th ed., McGraw–Hill, 1996, pp. 77–101.*
J.K. Scott et al., Science,"Searching for Peptide Ligands with an Epitope Library," Jul. 1990, vol. 249, pp. 386–390.*
Jean Cosme—Immunization reverses memory deficits without reducing brai AB burden in alzheimer's disease model (2002).*
Dave Morgan—AB peptide vaccination prvents memory loss inan animal model of Alzheimer's disease (2000).*
Christopher Janus—AB peptide immunization reduces behavioural impairment and plaques in a modelof alzheimer's disease.*
John Hardy and Dennis Selkoe—the Amyloid Hypothesis of Alzheimer's Disease: Progress and Problems on the Road to Therapeutics (2002).*
Erika Check—Nerve inflammation halts trial for Alzheimer's drug (2002).*
Work on weapons adds to public distrust of science (2002).*
Anne E. Willis et al, Immunological properties of foreign peptides in multiple display ona filamentous bacteriophage, Gene 128 (1993) 79–83.*

Smith, "Surface presentation of protein epitopes using bacteriophage expression systems", *Current Opinion in Biotechnology*, 2:668–673 (1991).
Renauld–Mongenie et al., "Induction of mucosal immune responses against a heterologous antigen fused to filamentous hemagglutinin after intranasal immunization with recombinant *Bordetella pertussis*", *Proc. Natl. Acad. Sci. USA*, 93:7944–7949 (1996).
Cesareni et al., "Minireview Peptides display on filamentous phage capsids a new powerful tool to study protein ligand interaction", *FEBS Letters*, 307:66–70 (1992).
Huse et al., "Application of a filamentous phage pVIII fusion protein system suitable for efficient production screening, and mutagenesis of F(ab) antibody fragments", *The Journal of Immunology*, (1992).
Jones et al., "Display of antibody chains on filamentous bacteriophage", *Methods in Molecular Biology*, 80:449–459.
Chang et al., "Expression of antibody Fab domains on bacteriophage surfaces potential use for antibody selection", *Journal of Immunology*, 147:3610–3614 (1991).
Glaser et al., "Antibody engineering by codon–based mutagenesis in a filamentous phage vector system", *The Journal of Immunology*, 149:3903–3913 (1992).
Hoogenboom et al., "Building antibodies from their genes", *Immunological Reviews*, 130–41–68 (1992).
Barbas et al., "Semisynthetic combinatorial antibody libraries: a chemical solution to the diversity problem", *Natl. Acad. Sci. USA*, 4457:4461 (1992).
Marks et al., "Molecular evolution of proteins of filamentous phage", *The Journal of Biological Chemistry*, 267:16007–16010 (1992).
Hawkins et al., "Selection of phage antibodies by binding affinity mimicking affinity maturation", *J. Mol. Biol.*, 226:889–896 (1992).
Wetzel, "Commentary learning from the immune system laboratory methods for creating and refining molecular diversity in polypeptides", *Protein Engineering*, 4:371–374 (1991).
Lerner et al., "Antibodies without immunization", *Science*, 258:1313–1314 (1992).

(List continued on next page.)

*Primary Examiner*—Deborah Crouch
(74) *Attorney, Agent, or Firm*—Browdy and Neimark, P.L.L.C.

(57) ABSTRACT

A strategy for immunizing against amyloid plaques using display technology. The strategy includes methods, agents, and pharmaceutical compositions for vaccination against plaque forming diseases (e.g. Alzheimer's disease) which rely upon presentation of an antigen or epitope on a display vehicle. The strategy further includes methods, agents, and pharmaceutical compositions for vaccination against plaque forming diseases (e.g. Alzheimer's disease) which rely upon presentation of an antibody, or an active portion thereof, on a display vehicle. Whether antigens or antibodies are employed, desegregation of plaques results from the immunization.

11 Claims, 21 Drawing Sheets

OTHER PUBLICATIONS

Barbas et al., "Recombinant human Fab fragments neutralize human type 1 immunodeficiency virus in vitro", *Proc. Natl. Acad. Sci. USA*, 89:9339–9343 (1992).

Zebedee et al., "Human combinatorial antibody libraries to hepatitis B surface antigen", *Proc. Natl. Acad. Sci. USA*, 89:3175–3179 (1992).

Gram et al., "In vitro selection and affinity maturation of antibodies from a naïve combinatorial immunoglobulin library", *Proc. Natl. Acad. Sci. USA*, 89:3576–3580 (1992).

Kang et al., "Antibody redesign by chain shuffling from random combinatorial immunoglobulin libraries", *Proc. Natl. Acad. Sci. USA*, 88:11120–11123 (1991).

Marks et al., "Molecular evolution of proteins on filamentous phage", *The Journal of Biological Chemistry*, 267:16007–16010 (1992).

Garrard et al., "Assembly and enrichment in a monovalent phage display system", *Biotechnology*, 9:1373–1377 (1991).

Goessling et al., "Enhanced degradation of the ferritin repressor protein during induction of ferritin messenger RNA translation", *Science*, 256:670 (1992).

Marks et al., "By–passing immunization human antibodies from V–gene libraries displayed on phage", *J. Mol. Biol.*, 222:581–597 (1991).

Clackson et al., "Letters to nature making antibody fragments using phage display libraries", *Nature*, 352:624–628 (1991).

Barbas et al., "Assembly of combinatorial antibody libraries on phage surfaces: The gene III site", *Proc. Natl. Acad. Sci. USA*, 88:7978–7982 (1991).

McCafferty et al., "Letters to nature phage antibodies: filamentous phage display antibody variable domains", *Nature*, 348:552–554 (1990).

Kang et al., "Linkage of recognition and replication functions by assembling combinatorial antibody Fab libraries along phage surfaces", *Proc. Natl. Acad. Sci. USA*, 88:4363–4366 (1991).

Burtion et al., "A large array of human monoclonal antibodies to type 1 human immunodeficiency virus from combinatorial libraries of asymptomatic seropositive individuals", *Proc. Natl. Acad. Sci. USA*, 88:10134–10137 (1991).

Breitling et al., "A surface expression vector for antibody screening", *Gene*, 104:147–153 (1991).

Hoogenboom et al., "Multi–subunit proteins on the surface of filamentous phage: methodologies for displaying antibody (Fab) heavy and light chains", *Nucleic Acids Research*, 19:4133–4137 (1991).

Barbas et al., "Human monoclonal Fab fragments derived from a combinatorial library bind to respiratory syncytial virus F glycoprotein and neutralize infectivity", *Proc. Natl. Acad. Sci. USA*, 89:10164–10168 (1992).

Somerville et al., "Immunodetection of PrP$^{SC}$ in spleens of some scrapie–infected sheep but not BSE–infected cows", *Journal of General Virology*, 7:2389–2396 (1997).

Frenkel et al., "N–terminal EFRH sequence of Alzheimer's β–amyloid peptide represents the epitope of its anti–aggregating antibodies", *Journal of Neroimmunology*, 88:85–90 (1998).

Schenk et al., "Letters of nature immunization with amyloid–β attenuates Alzheimer–disease–like pathology in the PDDAPP mouse", *Nature*, 400:173–177 (1999).

Solomon et al., "Monoclonal antibodies inhibit in vitro fibrillar aggregation of the Alzheimer β–amyloid peptide", *Proc. Natl. Acad. Sci. USA*, 93:452–455 (1996).

Solomon et al., "Disaggregation of Alzheimer β–amyloid by site–directed mAb", *Proc. Natl. Acad. Sci. USA*, 94:4109–4112 (1997).

Motti et al., "Recognition by human sera and immunogenicity of HbsAg mimotopes selected from an M13 phage display library", *Gene*, 146:191–198 (1994).

Hanan et al., "Inhibitory effect of monoclonal antibodies on Alzheimer's β–amyloid peptide aggregation", *Int. J. Exp. Clin. Invest.*, 3:130–133 (1996).

Meola et al., "Immunogenicity of filamentous phage displaying peptidemimotopes after oral administration", *Vaccine*, 15:1276–1285 (1997).

Delmastro, et al, "Immunogenicity of filamentous phage displaying peptide mimotopes after oral administration", *Vaccine*, 15:1276–1285 (1997).

Malik, et al., "Factors limiting display of foreign peptides on the major coat protein of filamentous bacteriophage capsids and a potential role for leader peptidase", *FEBS Letters*, 436:263–266 (1998).

Malik, et al, "Role of capsid structure and membrane protein processing in determining the size and copy number of peptides displayed on the major coat protein of filamentous bacteriophage", *J Mol Biol*,260:9–21 (1996).

Barinaga, M., "An Immunization Against Alzheimer's?", *Science*, 285(5425): 175–177, Jul. 9, 1999.

"Test of Alzheimer's Vaccine in Mice Shows Promise", *CNN Interactive*, Jul. 7, 1999.

Solomon et al, "Monoclonal Antibodies Inhibit in vitro Fibrillar Aggregation of the Alzheimer β–amyloid Peptide", *Proc. Natl. Acad. Sci. USA*, 93: 452–455, 1996.

Solomon et al, "Disaggregation of Alzheimer β–amyloid by Site–Directed mAB", *Proc. Natl. Acad. Sci.*, 94: 4109–4112.

Hanan et al, "Inhibitory Effect of Monoclonal Antibodies on Alzheimer β–amyloid Peptide Aggregation", *J. Exp. Clin. Invest.*, 3: 130–133, 1996.

Draghia et al, "Gene Delivery Into the Central Nervous System by Nasal Instillation in Rats", *Gene Therapy*, 2:418–423, 1995.

Frenkel et al, "N–Terminal EFRH Sequence of Alzheimer β–amyloid Peptide Represents the Epitope of its Anti–Aggregating Antibodies", *J. Neuroimmunology*, 88: 85–90, 1998.

* cited by examiner

FIG.1A
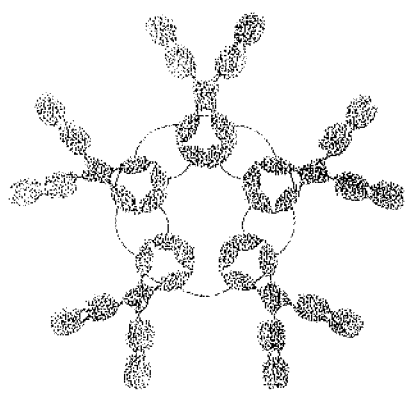
IgM 950Kd
FIG.1B
FIG.1C
750bp
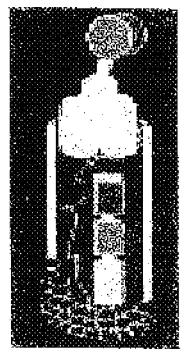
FIG.1D
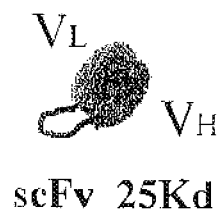
$V_L$ $V_H$
scFv 25Kd
FIG.1E

FIG. 11a

```
CAG GTC AAA CTG CAG GAG TCA GGG GCT GAG CTG GTG ACG CCT GGG GTC TCA GTG AAG ATT
gln val lys leu gln glu ser gly ala glu leu val arg pro gly val ser val lys ile TCC TGC AAG GGT TCT GGC TAC ACA TTC ACT GAT TAT GCT ATG AAC TGG GTG AAG CAG AGT
ser cys lys gly ser gly tyr thr phe thr asp tyr ala met his trp val lys gln ser
                                              CDR 1

CAT GCA AAG AGT CTA GAG TGG ATT GGA GTT ATT AGT ACT ACT TAC TAT GAT GCT AGC TAC
his ala lys ser leu glu trp ile gly val ile ser thr thr tyr tyr asp ala ser tyr
                                                                       CDR 2

AAC CAG AAG TTC AAG GGC AAG GCC ACA ATG ACT GTA GAC AAA TCC TCC AGC ACA GCC TAT
asn gln lys phe lys gly lys ala thr met thr val asp lys ser ser ser thr ala tyr
            CDR 2

ATG GAA CTT GCC AGA CTG ACA TCT GAG GAT TCT GCC ATC TAT TAC TGT GCA AGA GGG GCT
met glu leu ala arg leu thr ser glu asp ser ala ile tyr tyr cys ala arg gly ala
                                                                          CDR 3

ACT ATG TCC TAC TTT GAC TAC TGG GGC CAA GTC ACC ACG GTC ACC GTC TCC TCA ggt gga
thr met ser tyr phe asp tyr trp gly gln val thr thr val thr val ser ser gly gly
          CDR 3
```

FIG. 11b

```
ggc ggt tca ggc gga gtt ggc tct ggc ggt ggc gga tcg gac atc gag ctc act cag tct
gly gly ser gly gly val gly ser gly gly gly gly ser asp ile glu leu thr gln ser
                          Linker CCA GCA ATC ATG TCT GCA TCT CCA GGG GAG AAG GTC ACC ATG ACC TGC AGT GCC AGC TCA
pro ala ile met ser ala ser pro gly glu lys val thr met thr cys ser ala ser ser
                                                                         CDR 1

AGT ATA AGT TAC ATG CAC TGG TAT CAG CAG AAG CCA GGC ACC TCC CCC AAA AGA TGG ATT
ser ile ser tyr met his trp tyr gln gln lys pro gly thr ser pro lys arg trp ile
    CDR 1

TAT GAC ACA TCC AAA CTG GCT TCT GGA GTC CCT CGC TTC AGT GGC AGT GGG TCT GGG
tyr asp thr ser lys leu ala ser gly val pro ala arg phe ser gly ser gly ser gly
            CDR 2

ACC TCT TAT TCT CTC ACA ATC AGC AGC ATG GAG GCT GAA GAT GCT GCC ACT TAT TAC TGC
thr ser tyr ser leu thr ile ser ser met glu ala glu asp ala ala thr tyr tyr cys CAT CAG CCG AGT AGT TAC CCA TTC ACG TTC GGA GGG GGG GCC AAG CTG GAA ATA AAA
his gln pro ser ser tyr pro phe thr phe gly gly gly ala lys leu glu ile lys
        CDR 3
```

FILAMENTOUS BACTERIOPHAGE DISPLAYING AN β-AMYLOID EPITOPE

The present application claims benefit under 35 U.S.C. §119(e) of U.S. Provisional Patent Application No. 60/152,417, filed Sep. 3, 1999.

FIELD AND BACKGROUND OF THE INVENTION

The present invention relates to methods, agents and compositions for treating plaque-forming diseases, including, but not limited to, Alzheimer's disease. More particularly, these methods involve the use of (i) plaque derived antigens cloned and displayed on the surface of a display vehicle for in vivo elicitation of antibodies capable of preventing plaque formnation and of disaggregating existing plaques; and (ii) antibodies raised against plaque derived antigens, cloned and displayed on a display vehicle, and which are capable of preventing plaque formation and of disaggregating existing plaques. The present invention further relates to a method of targeting a display vehicle to the brain of an animal, including man.

Alzheimer's Disease—Clinical Overview:

Alzheimer's disease (AD) is a progressive disease resulting in senile dementia. Broadly speaking, the disease falls into two categories: late onset, which occurs in old age (typically above 65 years) and early onset, which develops well before the senile period, e.g., between 35 and 60 years. In both types of the disease, the pathology is similar, but the abnormalities tend to be more severe and widespread in cases beginning at an earlier age. The disease is characterized by two types of lesions in the brain, senile plaques and neurofibrillary tangles. Senile plaques are areas of disorganized neutrophils up to 150 mm across with extracellular amyloid deposits at the center, visible by microscopic analysis of sections of brain tissue. Neurofibrillary tangles are intracellular deposits of tau protein consisting of two filaments twisted about each other in pairs.

Senile Plaques and Other Amyloid Plaques:

The principal constituent of the senile plaques is a peptide termed Aβ or beta-amyloid peptide (βAP). The amyloid beta peptide is an internal fragment of 39–43 amino acids of a precursor protein termed amyloid precursor protein (APP). Several mutations within the APP protein have been correlated with the presence of Alzheimer's disease (See, e.g., Goate et al., Nature 349,704, 1991, valine$^{717}$ to isoleucine; Chartier Harlan et al. Nature 353, 844, 1991, valine$^{717}$ to glycine; Murrell et al., Science 254, 97, 1991, valine$^{717}$ to phenylalanine; Mullan et al., Nature Genet. 1, 345, 1992, a double mutation changing lysine$^{595}$-methionine$^{596}$ to asparagine$^{595}$-leucine$^{596}$).

Such mutations are thought to cause Alzheimer's disease by increased or altered processing of APP to beta-amyloid, particularly processing of APP to increased amounts of the long form of beta-amyloid (i.e., Aβ1-42 and Aβ1-43). Mutations in other genes, such as the presenilin genes, PS1 and PS2, are thought indirectly to affect processing of APP to generate increased amounts of long form beta-amyloid (see Hardy, TINS 20, 154, 1997). These observations indicate that beta-amyloid, and particularly its long form, is a causative element in Alzheimer's disease.

Amyloid deposits comprise a peptide aggregated to an insoluble mass. The nature of the peptide varies in different diseases but in most cases, the aggregate has a beta-pleated sheet structure and stains with Congo Red dye. In addition to Alzheimer's disease (AD), both late and early onset, other diseases characterized by amyloid deposits are, for example, SAA amyloidosis, hereditary Icelandic syndrome, multiple myeloma, and spongiform encephalopathies, including mad cow disease, Creutzfeldt Jakob disease, sheep scrapie, and mink spongiform encephalopathy (see, for example, Weissmann et al., Curr. Opin. Neurobiol. 7, 695–700, 1997; Smits et al., Veterinary Quarterly 19, 101–105, 1997; Nathanson et al., Am. J. Epidemiol. 145, 959–969, 1997).

The peptides forming the aggregates in these other diseases are serum amyloid A, cystantin C and IgG kappa light chain, respectively, for the first three, and prion protein for the others.

Other peptides or proteins with evidence of self aggregation are also known, such as, but not limited to, amylin (Young A A. et al., 1994, FEBS Lett, 343(3);237–41); bombesin, caerulein, cholecystokinin octapeptide, eledoisin, gastrin-related pentapeptide, gastrin tetrapeptide, somatostatin (reduced), substance P; and peptide, luteinizing hormone releasing hormone, somatostatin N-Tyr (Banks and Kastin, Prog Brain Res., 91:139–4, 1992).

Treatment:

U.S. Pat. No. 5,688,561 to Solomon teaches methods of identifying monoclonal antibodies effective in disaggregating protein aggregates and preventing aggregation of such proteins. Specifically, U.S. Pat. No. 5,688,561 demonstrates anti-beta-amyloid monoclonal antibodies effective in disaggregating beta-amyloid plaques and preventing beta-amyloid plaque formation in vitro. U.S. Pat. No. 5,688,561 stipulates the in vivo use of such antibodies to prevent plaque formation by aggregation of beta-amyloid or to disaggregate beta-amyloid plaques which have already formed. These teachings do not, however, identify an epitope to be employed to generate such antibodies. In addition, these teachings do not provide means with which to enable the penetration of such antibodies into the brain through the blood brain barrier (BBB). Furthermore, this patent fails to teach the use of phage display technology as a delivery method for antigens or antibodies. Yet furthermore no experimental results demonstrating the in vivo effectiveness of such antibodies are demonstrated by U.S. Pat. No. 5,688,561.

EP 526511 by McMichael teaches administration of homeopathic dosages (less than or equal to $10^{-2}$ mg/day) of beta-amyloid to patients with pre-established AD. In a typical human with about 5 liters of plasma, even the upper limit of this dosage would be expected to generate a concentration of no more than 2 pg/ml. The normal concentration of beta-amyloid in human plasma is typically in the range of 50–200 pg/ml (Seubert et al., Nature 359, 325–327 1992). Because this proposed dosage would barely alter the level of endogenous circulating beta-amyloid and because EP 526511 does not recommend the use of an adjuvant, it seems implausible that any therapeutic benefit would result therefrom.

PCT/US98/25386 by Schenk and a Nature paper by Schenk et al. (Nature, 400:173–177, 1999) teach administration of beta-amyloid immunogens to a patient in order to generate antibodies to prevent formation of plaques or dissolve existing plaques. According to Schenk, 50 to 100 mg of antigen are required, 1 to 10 mg if an adjuvant is employed. These teachings also stipulate that a similar effect may be achieved by direct administration of antibodies against beta-amyloid, in both cases disregarding the blood brain barrier which, under normal circumstances, prevents the penetration of antibodies into the brain.

It is also important to note that these teachings are typically restricted to the use of " . . . any of the naturally occurring forms of beta-amyloid peptide, and particularly the human forms (i.e., Aβ39, Aβ40, Aβ41, Aβ42 or Aβ43)" or " . . . longer polypeptides that include, for example, a beta-amyloid peptide, active fragment or analog together with other amino acids", or "multimers of monomeric immunogenic agents".

These teachings ignore, however, earlier data teaching that the first 28 amino acids of beta-amyloid are sufficient to elicit antibodies which both disaggregate and inhibit aggregation of beta-amyloid plaques in vitro (Hanan and Solomon, Amyloid: Int. J. Exp. Clin. Invest. 3:130–133, 1996; Solomon et al., Proc. Natl. Acad. Sci. U.S.A. 93:452–455, 1996; Solomon et al., Proc. Natl. Acad. Sci. U.S.A. 94:4109–4112, 1997).

Schenk and Schenk et al. both fail to teach the use of the N-terminal epitope of beta-amyloid plaques which is known to be a sequential epitope composed of only four amino acid residues (EFRH, SEQ ID NO:1) located at positions 3–6 of the beta-amyloid peptide (Frenkel D., J. Neuroimmunol., 88:85–90,1998). Antibodies against this epitope have subsequently been shown to disaggregate beta-amyloid fibrils, restore beta-amyloid plaques solubilization and prevent neurotoxic effects on PC 12 cells (Solomon, B. et al., Proc. Natl. Acad. Sci. USA. 94:4109–4112, 1997; and Solomon, B., et al., Proc. Natl. Acad. Sci. USA., 93:452–455,1996).

This epitope has been independently confirmed as the epitope bound by anti-aggregating antibodies using random combinatorial hexapeptide phage display (Frenkel and Solomon, J. of Neuroimmunol. 88:85–90, 1998).

The EFRH (SEQ ID NO:1) epitope is available for antibody binding when beta-amyloid peptide is either in solution or in aggregates. Blocking of this epitope by a monoclonal antibody prevents self-aggregation and enables resolubilization of already formed aggregates.

These findings suggest that the teachings of Schenk and colleagues are inefficient at best. Since, as has already been mentioned hereinabove, the normal concentration of beta-amyloid in human serum is 50–200 pg/ml, immunization with that peptide could be expected to produce either low antibody titers or high toxicity if strong adjuvants are used and as such it is not applicable for therapy. Indeed, in order to achieve significant serum titers of antibody against beta-amyloid a series of 11 monthly injections was required (Schenk et al., Nature, 400:173–177, 1999). The degree to which these serum titers will persist over time is not yet known, and this point is especially crucial with respect to early onset Alzheimer's disease.

Schenk and colleagues further teach that an immunogenic peptide such as beta-amyloid may be displayed upon the surface of a virus or bacteria. However, they fail to teach use of an antigen so displayed to effect immunization. No mention is made of defining an epitope in this context and no experimental data is provided either. In addition, delivery of antibody displayed on a display vehicle is not taught by Schenk or Schenk et al. altogether.

Collectively, the prior art fails to teach means with which an effective titer of anti-aggregation antibodies can be generated in vivo in a short time and/or be introduced into the brains of patients suffering a plaque-forming diseases. In addition, the persistence of titers generated via prior art teachings has not been established.

There is thus a widely recognized need for, and it would be highly advantageous to have, effective means of disaggregating amyloid plaques in vivo which would have lasting effect, high efficiency, rapid onset, no adverse effect on the treated subject and which is readily amenable to large scale production.

SUMMARY OF THE INVENTION

According to one aspect of the present invention there is provided a method of treating a plaque forming disease comprising the steps of (a) displaying a polypeptide on a display vehicle, the polypeptide representing at least one epitope of an aggregating protein associated plaque formation in the plaque forming disease, the at least one epitope being capable of eliciting antibodies capable of disaggregating the aggregating protein and/or of preventing aggregation of the aggregating protein; and (b) introducing the display vehicle into a body of a recipient so as to elicit the antibodies capable of disaggregating the aggregating protein and/or of preventing aggregation of the aggregating protein.

According to another aspect of the present invention there is provided an agent for treating a plaque forming disease comprising a displayvehicle displaying a polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein.

According to yet another aspect of the present invention there is provided a pharmaceutical composition for treating a plaque forming disease comprising an effective amount of a display vehicle displaying a polypeptide, the polypeptide representing at least one epitope of an aggregating protein associated with plaque formation in the plaque forming disease, the at least one epitope being capable of eliciting an effective amount of antibodies capable of disaggregating the aggregating protein and/or of preventing aggregation of the aggregating protein, the pharmaceutical composition further comprising a pharmaceutically acceptable carrier.

According to still another aspect of the present invention there is provided a method of preparing a display vehicle for treating a plaque forming disease, the method comprising the step of genetically modifying a genome of a display vehicle by inserting therein a polynucleotide sequence encoding a polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein, such that when the display vehicle propagates the polypeptide is displayed by the display vehicle.

According to an additional aspect of the present invention there is provided a method of treating a plaque forming disease comprising the steps of (a) displaying a polypeptide representing at least an immunological portion of an antibody being for binding at least one epitope of an aggregating protein associated with plaque formation in the plaque forming disease, the binding capable of disaggregating the aggregating protein and/or of preventing aggregation of the aggregating protein; and (b) introducing the display vehicle into a body of a recipient so as to disaggregate the aggregating protein and/or prevent its aggregation.

According to still an additional aspect of the present invention there is provided a method of introducing a display vehicle lacking an engineered targeting moiety into a brain of a recipient, the method comprising the step of administering the display vehicle intranasally to the recipient.

According to further features in preferred embodiments of the invention described below, the step of introducing the display vehicle into the body of the recipient so as to disaggregate the aggregating protein is effected through an olfactory system of the recipient.

According to yet another additional aspect of the present invention there is provided an agent for treating a plaque forming disease comprising a display vehicle displaying a polypeptide representing at least an immunological portion of an antibody which can bind at least one epitope of an aggregating protein associated with plaque formation in the plaque forming disease, the immunological portion of the antibody being capable of disaggregating said aggregating protein and/or of preventing aggregation of the aggregating protein.

According to yet an additional aspect of the present invention there is provided a pharmaceutical composition for treating a plaque forming disease comprising an effective amount of a display vehicle displaying a polypeptide representing at least an immunological portion of an antibody which can bind at least one epitope of an aggregating protein associated with plaque formation in the plaque forming disease, the immunological portion of the antibody being capable of disaggregating the aggregating protein and/or of preventing aggregation of the aggregating protein, the pharmaceutical composition further comprising a pharmaceutically acceptable carrier.

According to still an additional aspect of the present invention there is provided a method of preparing a display vehicle for treating a plaque forming disease comprising the step of genetically modifying a genome of a display vehicle by inserting therein a polynucleotide sequence encoding at least an immunological portion of an antibody capable of binding at least one epitope of an aggregating protein associated with plaque formation in the plaque forming disease, the immunological portion of the antibody being capable of disaggregating the aggregating protein and/or of preventing aggregation of the aggregating protein.

According to further features in preferred embodiments of the invention described below, the plaque forming disease is selected from the group consisting of early onset Alzheimer's disease, late onset Alzheimer's disease, presymptomatic Alzheimer's disease, SAA amyloidosis, hereditary Icelandic syndrome, senility, multiple myeloma and a spongiform encephalopathy.

According to still further features in the described preferred embodiments, the aggregating protein is selected from the group consisting of beta-amyloid, serum amyloid A, cystanin C, IgG kappa light chain and prion protein.

According to additional further features in preferred embodiments of the invention, the display vehicle is selected from the group consisting of a double stranded DNA virus, a single stranded DNA virus, an RNA virus, a bacteria and a prion.

According to still further features in the described preferred embodiments, the display vehicle is a virus.

According to still further features in the described preferred embodiments, the display vehicle is a bacteriophage.

According to still further features in the described preferred embodiments, the display vehicle is a filamentous bacteriophage.

According to further features in described preferred of the invention, the bacteriophage display vehicle is capable of propagating within bacterial flora of the host.

According to further features in described preferred embodiments of the invention, the bacteriophage display vehicle is capable of propagating within $E.\ coli$.

According to still further features in the described preferred embodiments the bacteriophage display vehicle is fd.

According to further features in described preferred embodiments of the invention, the display vehicle is incapable of propagation in vivo.

According to still further features in the described preferred embodiments, a triple dose of $10^{10}$ units of the chosen display vehicle induces an antibody titer of at least 1:50,000 within 30 days of administration, as measured by ELISA. The present invention successfully addresses the shortcomings of the presently known configurations by providing methods, agents, and pharmaceutical compositions for quickly and reliably preventing or reversing the progression of a plaque forming disease. The invention further includes methods for preparing display vehicles for use as agents, or as part of pharmaceutical compositions, associated with prevention or reversal of plaque forming diseases.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments. of the present invention only, and are presented in the cause of providing what is believed to be the most useful and readily understood description of the principles and conceptual aspects of the invention. In this regard, no attempt is made to show details of the invention in more detail. than is necessary for a fundamental understanding of the invention, the description taken with the drawings making apparent to those skilled in the art how the several forms of the invention may be embodied in practice.

In the drawings:

FIG. 1$a$ is a schematic depiction of an IgM antibody.

FIG. 1$b$ is a photograph of an ethidium bromide stained 1.5% agarose gel showing cDNA fragments of the heavy and the light chains of IgM508. Lane 1: Kb (Ladder); Lanes 2 and 3 $V_H$ and $V_L$ fragments, respectively, as indicated by arrows.

FIG. 1$c$ is a photograph of an ethidium bromide stained 1.5% agarose gel showing scFv DNA fragment derived from antibody IgM 508. Lane 1: Kb (Ladder); Lane 2: scFv 508 DNA (750 bp).

FIG. 1$d$ is a schematic depiction of filamentous phage displaying an scFv.

FIG. 1$e$ is a schematic depiction of a soluble scFv.

FIGS. 11*a* and 11*b* show nucleotide (SEQ ID NO:5) and deduced amino acid (SEQ ID NO:6) sequences of scFv 508F heavy chain (FIG. 11*a*); and the linker and the variable region of the light chain (FIG. 11*b*) (SEQ ID NOs:25 and 26). The amino acid sequence is presented by a three-letter code; CDRs and the linker are underlined.

DESCRIPTION OF THE PREFERRED EMBODIMENTS

Figure 2:
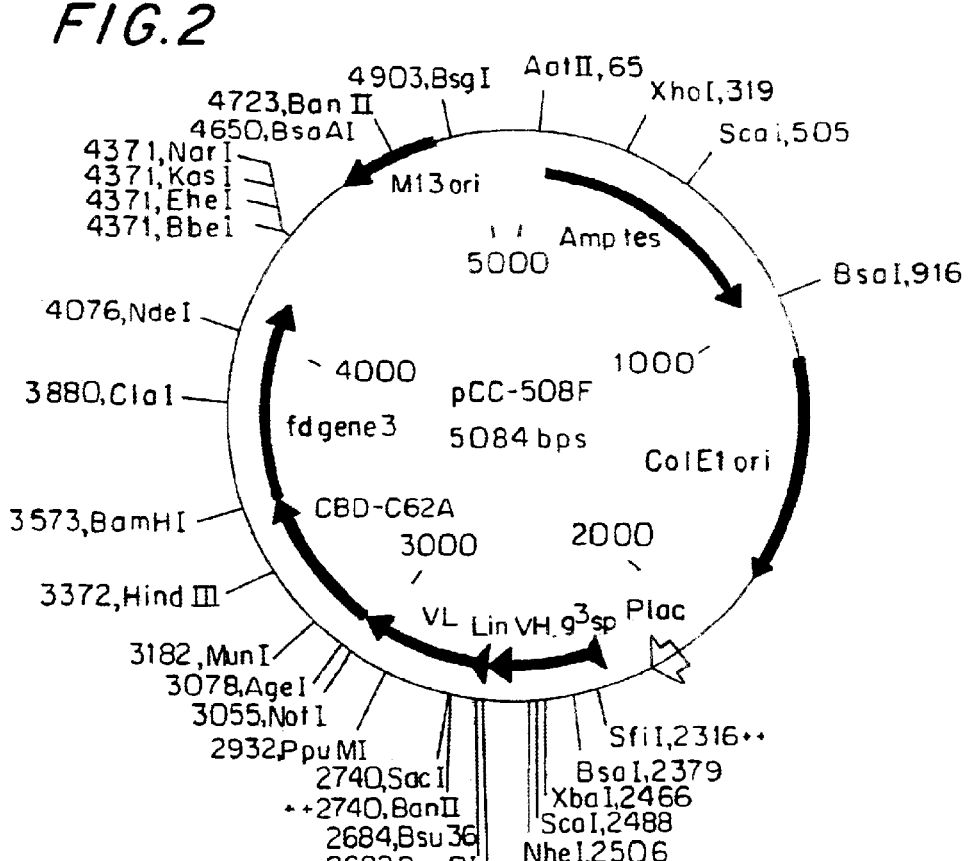
FIG. 2 is a physical map of plasmid pCC-508F which is used for the production of scFv-508-CBD fusion protein (also referred to herein as 508(Fv)-CBD) under control of lac promoter. Amp res—a gene encoding (β-lactamase; $V_H$ and $V_L$—sequences coding for the variable domains of the heavy and light chains of scFv-508, respectively; Lin—a gene coding for a (Gly4Ser)3 (SEQ ID NO:2) linker present between the variable domains $V_H$ and $V_L$. Restriction sites and positions thereof are also shown.

The present invention is of methods, pharmaceutical agents and compositions which can be used for treating plaque-forming diseases, including, but not limited to, Alzheimer's disease. Specifically the present invention can be used to (i) induce active immunity to plaque derived antigens in a recipient by immunizing with at least one epitope of an aggregating protein associated with plaque formation in a plaque forming disease on a display vehicle, so that antibodies elicited in response to immunization are capable of preventing plaque formation and/or of disaggregating existing plaques; and (ii) induce passive immunity by administering at least an immunological portion of an antibody which can bind to at least one epitope of an aggregating protein associated with plaque formation in a plaque forming disease, raised against plaque derived antigens, cloned and displayed on a display vehicle, capable of preventing plaque formation and of disaggregating existing plaques. This passive immunity may be of exceptionally long duration if the display vehicle employed is capable of replicating within the recipient. The present invention further relates to a method of targeting a display vehicle to the brain of an animal, including man, so that plaques present in the brain, such as beta amyloid plaques in brains of Alzheimer's disease patients, may be disaggregated.

The principles and operation of immunization according to the present invention may be better understood with reference to the drawings and accompanying descriptions.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

While reducing one aspect of the present invention to practice, as is further exemplified in the Examples section that follows, antigens derived from beta amyloid peptide were displayed on the surface of a filamentous phage which was used for immunization of experimental animals. All of the peptides employed contained the EFRH epitope (SEQ ID NO:1, residues 3–6, SEQ ID NO:3) of beta amyloid peptide (SEQ ID NO:3). The epitope was presented as a fusion protein of fd phage coat glycoprotein III or VIII. Doses ranging from $10^{10}$ to $10^{12}$ phages per injection were employed on 8 week old female BALB/c mice. A typical immunization schedule included three injections at 14-day intervals, administered either intraperitoneally or intranasally.

During and after the immunization process, the antibody serum titer of subject mice was tested for the production of Aβ specific antibodies by enzyme linked immunosorbent assay (ELISA) as detailed in methods and materials hereinbelow. Serum titers were subsequently shown to persist for 11 months in response to a protocol including only 3 immunizations. While all tested epitopes containing EFRH produced a titer, displaying the epitope on the surface of a display vehicle produced far highest and unexpected titers. These high titers are believed to be a result of the great number of copies presented to the immune system using this method, and this idea is supported by results of binding assays using controlled amounts of sera.

The anti-aggregating properties of the obtained polyclonal antibody raised against EFRH epitopes with respect to beta-amyloid fibril formation was measured by the ThT binding assay. Serum, at dilution of 1:10 and 1:100, disrupted formation of fibril structure of β-amyloid with extensive deterioration of fibril morphology, as indicated by a substantial decrease in ThT fluorescence. The unrelated serum used as control (serum from un-immunized mouse) did not significantly inhibit fibril formation.

The effect of the same serum on disruption of already formed βA fibril (the toxic form of βAP) was also determined. Serum of EFRH immunized mice incubated with pre-formed βA fibrils disrupted the fibril structure. The unrelated control antibody had no significant effect on fibril morphology. Together, these results confirm the ability of EFRH epitope presented by suitable display vehicles to evoke production of anti-aggregation antibodies which can inhibit or reverse the process of fibril formation.

Diluted serum produced according to this embodiment of the present invention prevented the neurotoxicity of beta amyloid peptide. This result implies potential clinical utility in preventing brain deterioration of patients suffering from amyloid plaque diseases.

Thus, according to one aspect of the present invention there is provided a method of treating a plaque forming disease. The method according to this aspect of the present invention is effected by displaying a polypeptide on a display vehicle, the polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein, and introducing the display vehicle into a body of a recipient, so as to elicit the antibodies capable of disaggregating the aggregating protein and/or of preventing aggregation of the aggregating protein.

According to a preferred embodiment of the present invention the display vehicle is selected such that less than 30 days following an introduction of a triple dose of $10^{10}$ units thereof to the recipient, a titer of the antibodies in the recipient is above 1:50,000, as is determined by ELISA.

According to another aspect of the present there is provided an agent for treating a plaque forming disease. The agent according to this aspect of the present invention comprising a display vehicle displaying a polypeptide, the polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein.

According to still another aspect of the present invention there is provided a pharmaceutical composition for treating a plaque forming disease. The composition according to this aspect of the present invention comprising an effective amount of a display vehicle displaying a polypeptide, the polypeptide representing at least one epitope of an aggregating protein associated with plaque formation in the plaque forming disease, the at least one epitope being capable of eliciting an effective amount of antibodies capable of disaggregating the aggregating protein and/or of preventing aggregation of the aggregating protein, and a pharmaceutically acceptable carrier.

According to yet another aspect of the present invention there is provided a method of preparing a display vehicle for treating a plaque forming disease. The method according to this aspect of the present invention is effected by genetically modifying a genome of a display vehicle by inserting therein a polynucleotide sequence encoding a polypeptide representing at least one epitope of an aggregating protein associated with plaque formation in the plaque forming disease, the at least one epitope being capable of eliciting antibodies capable of disaggregating the aggregating protein and/or of preventing aggregation of the aggregating protein, such that when the display vehicle propagates the polypeptide is displayed by the display vehicle.

Use of beta amyloid peptide antigens in conjunction with adjuvants to effect immunization has previously been difficult due to a combination of high toxicity and low titers which result. Using prior art methods as a starting point, immunization of a mouse with a 16 amino acids peptide of beta-amyloid conjugated to KLH (SEQ ID NO:9) was carried out. This immunization produced a low but measurable antibody titer against beta-amyloid.

While reducing another aspect of the present invention to practice, splenectomy of the immunized mouse facilitated preparation of IgM hybridoma 508 expressing scFvAb with specificity to beta-amyloid. RNA was subsequently extracted from this hybridoma and was employed for antibody cloning. IgM 508 hybridoma showed specific activity to AP in preventing its toxic affect on PC12 cells (Anavi, S. 1998, M. Sc. thesis from the department of Molecular Microbiology and Biotechnology of the Tel-Aviv University, Israel). $V_H$ and $V_L$ sequences of IgM 508 were cloned separately and linked using a commercially available vector to form a single chain antibody with anti-beta amyloid specificity. This single chain antibody was subsequently expressed as a fusion protein in a phage display library and clones with anti beta amyloid activity were selected for propagation in E. coli.

Further reduction to practice was demonstrated by determining the apparent binding constants of the purified antibody presenting phage to amyloid beta were measured by ELISA test, and half-maximal binding was obtained at an antibody concentration of 340 ng/ml, corresponding to $8 \times 10^{-6}$ M. This result anticipate that the prepared single chain antibody will be effective under in vivo conditions. This phage was also able to disrupt already formed fibril structures confirming that the purified single chain antibody is biologically active, as suggested by the binding constant determination.

Thus, according to an additional aspect of the present invention there is provided a method of treating a plaque forming disease. The method according to this aspect of the present invention is effected by displaying a polypeptide representing at least an immunological portion of an antibody being for binding at least one epitope of an aggregating protein associated with plaque formation in the plaque forming disease, the binding capable of disaggregating the aggregating protein and/or of preventing aggregation of the aggregating protein, and introducing the display vehicle into a body of a recipient so as to disaggregate the aggregating protein and/or prevent its aggregation.

According to a preferred embodiment of the present invention, and as is further described hereinbelow and exemplified hereinunder in the Examples section, introducing the display vehicle into the body of the recipient so as to disaggregate the aggregating protein and/or prevent the aggregation of the aggregating protein is effected through an olfactory system of the recipient.

According to yet an additional aspect of the present invention there is provided an agent for treating a plaque forming disease. The agent according to this aspect of the present invention comprising a display vehicle displaying a polypeptide representing at least an immunological portion of an antibody which can bind at least one epitope of an aggregating protein associated with plaque formation in the plaque forming disease, the immunological portion of the antibody being capable of disaggregating said aggregating protein and/or of preventing aggregation of the aggregating protein.

According to still an additional aspect of the present invention there is provided a pharmaceutical composition for treating a plaque forming disease. The composition according to this aspect of the present invention comprising an effective amount of a display vehicle displaying a polypeptide representing at least an immunological portion of an antibody which can bind at least one epitope of an aggregating protein associated with plaque formation in the plaque forming disease, the immunological portion of the antibody being capable of disaggregating the aggregating protein, and a pharmaceutically acceptable carrier.

According to a further aspect of the present invention there is provided a method of preparing a display vehicle for treating a plaque forming disease. the method according to this aspect of the present invention is effected by genetically modifying a genome of a display vehicle by inserting therein a polynucleotide sequence encoding at least an immunological portion of an antibody capable of binding at least one epitope of an aggregating protein associated with plaque formation in the plaque forming disease, the immunological portion of the antibody being capable of disaggregating the aggregating protein.

For purposes of this specification and the accompanying claims the terms "patient", "subject" and "recipient" are used interchangeably. They include humans and other mammals which are the object of either prophylactic, experimental, or therapeutic treatment.

For purposes of this specification and the accompanying claims, the terms "beta amyloid peptide" is synonymous with "β-amhyloid peptide", "βAP", "βA", and "Aβ". All of these terms refer to a plaque forming peptide derived from amyloid precursor protein.

As used herein in the specification and in the claims the term "disaggregating" refers to solubilization of aggregated proteins. Aggregated βP, for example, is a mixture of oligomers in which the monomeric units are held together by non covalent bonds.

For purposes of this specification and the accompanying claims the terms "comprising" refers to inclusion of one or more recited element but does not exclude other elements not specifically recited. For example, a composition that comprises Aβ peptide encompasses both an isolated Aβ peptide and Aβ peptide as a component of a larger polypeptide sequence. Similarly, an immunological portion of an antibody may be included as a part of a larger of the antibody, say the entire antibody.

As used herein in the specification and in the claims section that follows, the term "treating" includes substantially inhibiting, slowing or reversing the progression of a disease, substantially ameliorating clinical symptoms of a disease or substantially preventing the appearance of clinical symptoms of a disease.

As used herein in the specification and in the claims section that follows, the term "plaque forming disease" refers to diseases characterized by formation of plaques by an aggregating protein (plaque forming peptide), such as, but not limited to, beta-amyloid, serum amyloid A, cystanin C, IgG kappa light chain or prion protein, in diseases such as, but not limited to, early onset Alzheimer's disease, late onset Alzheimer's disease, presymptomatic Alzheimer's disease, SAA amyloidosis, hereditary Icelandic syndrome, senility, multiple myeloma or spongiform encephalopathy.

Because amyloid plaques associated with the diseases described hereinabove are located within the brain, any proposed treatment modality must demonstrate an ability to cross the blood brain barrier (BBB) as well as an ability to dissolve amyloid plaques. Normally, the average size of molecules capable of penetrating the BBB is approximately 2 kDa. Monoclonal antibodies are typically in the range 135–900 kDa. Therefore, future therapeutic use of antibodies in treating amyloid plaque diseases must rely on either reduction of their size concurrent with retention of activity, or on development of novel delivery strategies.

Small synthetic peptides consisting of antigen epitopes, such as the EFRH (SEQ ID NO:1) epitope of Aβ described hereinbelow, are in general poor antigens and need to be coupled to a larger carrier. Even after coupling they may induce only a low affinity immune response. Injection of Aβ-KLH or Aβ-fibril leads to very slow immune response (Anavi, S., 1998, M. Sc. thesis from the Department of Molecular Microbiology and Biotechnology of the Tel-Aviv University) and many efforts have been made to circumvent low affinity response, with limited success.

Since the pathological effects of amyloid beta fibril in AD patients are maintained only in the central nervous system (CNS), the capability of highly specific InAbs in preventing Amyloid beta fibril toxicity in vivo tests is dependent on the permeability of the blood brain barrier (BBB). In the progressive stage of AD, evidence shows alteration in the permeability of the BBB, which may lead to direct delivery of such antibody from the periphery to the CNS to disaggregate already formed plaques and minimize further toxic effects (Schenk et al., Nature 1999, 100:173–177). Preferred embodiments of the present invention include such direct delivery of scFv Ab presented on display vehicles to the brain. across the blood brain barrier.

An increasing body of evidence shows that olfactory deficits and degenerative changes in the central olfactory pathways are affected early in the clinical course of AD. Moreover, the anatomic patterns involved in AD suggest that the olfactory pathway may be the initial stage in the development of AD.

Olfactory receptor neurons are bipolar cells that reside in the epithelial lining of the nasal cavity. Their axons traverse the cribriform plate and project to the first synapse of the olfactory pathway in the olfactory pathway in the olfactory bulb of the brain. This configuration makes them a highway by which viruses or other transported substances may gain access to the CNS across the BBB. In the early stages of AD the BBB may limit the entry of antibody circulating in the periphery to the CNS. In contrast Aβ anti-aggregating antibodies displayed on a phage surface have the potential not only be delivered directly to the CNS by intranasal administration but also to prevent olfactory permanent damage by βA in the patients. As previously shown, intranasal administration (Mathison et al., J. Drug Target, 1998) 5(6), 415–441; Chou et al., Biopharm Drug Dispos. 1997) 18(4): 335–46; et al., Gene Therapy 1995) 2:418–423) enables the direct entry of viruses and macromolecules into the CSF or. CNS.

Use of olfactory receptor neurons as a point of delivery for an adenovirus vector to the brain is reported in the literature. This method reportedly causes expression of a reporter gene in the brain for 12 days without apparent toxicity (Draghia et al., Gene Therapy 2:418–423, 1995).

Thus, according to a preferred embodiment of the present invention, a vehicle displaying an immunological portion of an antibody as herein described is delivered via this route to the brain.

As Aβ is produced continuously by cells in peripheral tissues which cross the blood brain barrier (BBB) leading to localized toxic effects in specific neuronal populations, intranasal administration of such a vehicle may also prevent the progression of the disease by minimizing the amount of peripheral Aβ available to form plaques.

The use of display vehicles such as filamentous phages as a drug delivery system to the CNS opens new horizons for therapeutic approaches for Alzheimer's disease, as well as for other neurodegenerative diseases involving toxic extracellular aggregation of human peptides.

The display vehicle according to the present invention can be of any type including viral (e.g., bacteriophage, such as filamentous bacteriophage, fd, for example), bacterial and prion display vehicles. Thus, for example, the display vehicle can be a double stranded DNA virus, a single stranded DNA virus, an RNA virus, a bacteria and a prion. According to a preferred embodiment of the present invention the display vehicle is capable of propagation in the recipient. Thus, for example, a bacteriophage display vehicle can be propagated in bacterial flora, such as *Escherichia coli* residing in the recipient's body. Alternatively, the display vehicle is an in vivo non-propagateable particle.

The phage or virus vehicle has promise as a targetable in vivo therapy approach. Although concerns about the potential infection of the natural intestinal flora (Delmastro et al., Vaccine 1997, 15: 1276–1285; Willis et al., Gene. 1993, 128:79–83; Poul et al., J. Mol. Biol. 1999, 288, 203–211) have been expressed, UV inactivation of phage showed (Delmastro et al., Vaccine 1997, 15: 1276–1285) that they are as immunogenic as their infective counterparts. Use of inactivated phage may preclude incorporation of phage encoded transgenes into the nucleus for subsequent expression in host cells (Larocca et al., 1998, Hum. Gene Ther. 9:2393–2399), an important practical consideration. Therefore, according to alternate preferred embodiments, the display vehicles employed in the present invention may be either replicating or non-replicating.

Phage or virus display involves the expression of cDNA clones as fusion proteins with phage or virus coat proteins. If the cDNAs selected for expression encode antigens, the phage or virus may then be employed as an antigen presenting vehicle, which can optionally replicate within a recipient.

As described above, according to preferred embodiments of the present invention, antigens displayed by a phage or virus may be used directly for vaccination, without antigen purification. In this case, the bulk of the coat proteins serve to stimulate a general immune response because they are "non-self" with respect to the vaccinated subject. The antigen-coat protein fusion elicits a specific antibody against epitopes in the displayed cDNA gene product.

Antibody phage or virus display is accomplished, for example, by fusing the coding sequence of the antibody variable regions to a phage or virus coat protein. To this end, the variable (V) regions ($V_H$ and $V_L$) rnRNA isolated from antibody-producing cells is reverse-transcribed into cDNA, and heavy and light chains assembled randomly to encode single chain Fv (scFv). These cassettes are cloned directly into a suitable vector such as a phagemid vector for expression and display on the phage or virus surface. This linkage between antibody genotype and phenotype allows the enrichment of antigen specific phage or virus antibodies, using immobilized or labeled antigen. Phage or virus that display a relevant antibody will be retained on a surface coated with antigen, while non-adherent phages or viruses will be washed away. Bound phages or viruses can be recovered from the surface, re-infected into suitable host cells and re-grown for further enrichment and, eventually for binding analysis.

The success of antibody phage or virus display hinges on the combination of this display and enrichment method. Phage or virus antibody genes can be sequenced, mutated and screened to improve antigen binding.

It is possible to rearrange the genes which code for the various regions of an antibody molecule such that its specificity and affinity for an antigen are altered. The antibody can be maintained on the surface of the phage or virus for further manipulation or be released as soluble scFv (~25 kDa) fragment.

Since its invention at the beginning of the 1990's, antibody phage display has revolutionized the generation of monoclonal antibodies and their engineering. This is because phage display allows antibodies to be made completely in vitro, bypassing the immune system and the immunization procedure, and allowing in vitro tailoring of the affinity and specificity of the antibody. It is therefore anticipated that the most efficient new vaccine development strategies will employ this technology.

Additional features can be added to the vector to ensure its safety and/or enhance its therapeutic efficacy. Such features include, for example, markers that can be used to negatively select against cells infected with the recombinant virus such as antibiotic sensitivity. Negative selection is therefore a means by which infection can be controlled because it provides inducible suicide through the addition of antibiotic. Such protection ensures that if, for example, mutations arise that produce altered forms of the viral vector or recombinant sequence, cellular transformation will not occur. Features that limit expression to particular cell types can also be included. Such features include, for example, promoter and regulatory elements that are specific for the desired cell type.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell.

As used herein in the specification and in the claims section that follows, the term polypeptide refers to a stretch of amino acids covalently linked there amongst via peptide bonds. Different polypeptides have different iunctionalities according to the present invention. While according to one aspect a polypeptide is derived from an immunogen designed to induce an active immune response in a recipient, according to another aspect of the invention, a polypeptide is derived from an antibody which results following the elicitation of an active immune response, in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a beneficial humoral (antibody mediated) and/or a cellular (mediated by antigen-specific T cells or their secretion products) response directed against an aggregating protein (plaque forming peptide) in a recipient patient. Such a response can be an active response induced by administration of immunogen or a passive response induced by administration of antibody or primed T-cells. A cellular immune response is elicited by the presentation of polypeptide epitopes in association with Class I or Class II MHC molecules, to activate antigen-specific $CD4^+$ T helper cells and/or $CD8^+$ cytotoxic T cells. The response may also involve activation of monocytes, macrophages, NK, cells, basophils, dendritic cells, astrocytes, microglia cells, eosinophils or other components of innate immunity.

As used herein "active immunity" refers to any immunity conferred upon a subject by administration of an antigen.

As used herein "passive immunity" refers to any immunity conferred upon a subject without administration of an antigen. "Passive immunity" therefore includes, but is not limited to, administration of a replicating display vehicle which includes an immunological portion of an antibody presented on its surface to a recipient. Although replication of such a vehicle is active, the immune response is passive from the standpoint of the recipient.

For purposes of this specification and the accompanying claims the terms "epitope" and "antigenic determinant" are used interchangeably to refer to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8–10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed. (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13–15 amino acids for CD4 cells. T cells that recognize the epitope can be identified by in vitro assays that measure antigen-dependent proliferation, as determined by $^3$H-thymidine incorporation by primed T cells in response to an epitope (Burke et al., J. Inf. Dis. 170, 1110–19, 1994), by antigen-dependent killing (cytotoxic T lymphocyte assay, Tigges et al., J. Immunol. 156, 3901–3910) or by cytokine secretion.

The presence of a cell-mediated immunological response can be determined by proliferation assays (CD4$^+$ T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific. Previous experience has shown that standard production of polyclonal antibodies is not the method of choice for preparation of disaggregating antibodies for plaque forming peptides due to problems of poor titer and toxicity.

In order to produce monoclonal antibodies hyperimmunization of an appropriate donor, generally a mouse, with the antigen is undertaken. Isolation of splenic antibody producing cells is then carried out. These cells are fused to a cell characterized by immortality, such as a myeloma cell, to provide a fused cell hybrid (hybridoma) which can be maintained in culture and which secretes the required monoclonal antibody. The cells are then be cultured, in bulk, and the monoclonal antibodies harvested from the culture media for use. By definition, monoclonal antibodies are specific to a single epitope. Monoclonal antibodies often have lower affinity constants than polyclonal antibodies raised against similar antigens for this reason.

Monoclonal antibodies may also be produced ex-vivo by use of primary cultures of splenic cells or cell lines derived from spleen (Anavi, S., 1998. Locking the N-terminal of the Alzheimer β-amhyloid peptide prevents the neurotoxicity in cell cultures, M. Sc. thesis. In order to produce recombinant antibody (see generally Huston et al, 1991; Johnson and Bird, 1991; Mernaugh and Memaugh, 1995), messenger RNAs from antibody producing B-lymphocytes of animals, or hybridoma are reverse-transcribed to obtain complementary DNAs (cDNAs). Antibody cDNA, which can be full length or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. For a general discussion of conjugation of fluorescent or enzymatic moieties see Johnstone & Thorpe, Immunochemistry in Practice, Blackwell Scientific Publications, Oxford, 1982. The binding of antibodies to a solid support substrate is also well known in the art. See for a general discussion Harlow & Lane Antibodies: A Laboratory Manual, Cold Spring Harbor Laboratory Publications, New York, 1988 and Borrebaeck, Antibody Engineering—A Practical Guide, W. H. Freeman and Co., 1992.

As used herein and in the claims, the phrase "an immunological portion of an antibody" include an F(ab')$_2$ fragment of an antibody, an Fab fragment of an antibody, an Fv fragment of an antibody, a heavy chain of an antibody, a light chain of an antibody, an unassociated mixture of a heavy chain and a light chain of an antibody, a heterodimer consisting of a heavy chain and a light chain of an antibody, a catalytic domain, of a heavy chain of an antibody, a catalytic domain of a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

As used herein the term "adjuvant" refers to a compound that, when administered in conjunction with an antigen, augments the immune response to the antigen, but when administered alone does not generate an immune response to the antigen. Adjuvants can augment an immune response by several mechanisms including lymphocyte recruitment, stimulation of B and/or T cells, and stimulation of macrophages.

A pharmaceutical preparation according to the present invention includes, as an active ingredient, a display vehicle displaying at least one epitope of an aggregating protein associated with plaque formation in a plaque forming disease, the at least one epitope being capable of eliciting antibodies capable of disaggregating the aggregating protein. Alternatively, a pharmaceutical composition according to the present invention includes, as an active ingredient, a display vehicle displaying at least an immunological portion of an antibody being for binding at least one epitope of an aggregating protein associated with plaque formation in said plaque forming disease, said immunological portion of said antibody being capable of disaggregating said aggregating protein.

The preparation according to the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the preparation accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer a preparation in a local rather than systemic manner, for example, via injection of the preparation directly into the brain of a patient.

Pharmaceutical compositions of the present invention may be manufactured by processes well known in the art, e.g., by means of conventional mixing, dissolving, granulating, dragee-making, levigating; emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired. disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continues infusion. Formulations for injection may be presented in unit dosage form, e.g., in ampoules or in multidose containers with optionally, an added preservative. The compositions may be suspensions, solutions or emulsions in oily or aqueous vehicles, and may contain fornulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma or brain levels of antibodies which are sufficient to prevent aggregation or disaggregate existing aggregates (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels above the MEC for 10–90% of the time, preferable between 30–90% and most preferably 50–90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Ausubel et.al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal; B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Reference is made to the following materials and methods, which were employed in experiments described in the following examples.

MATERIALS AND EXPERIMENTAL METHODS

The following materials and experimental methods were employed while reducing the present invention to practice as is further demonstrated in the Examples that follow:
General Recombinant DNA and Phage Techniques:

Standard recombinant DNA techniques were performed essentially as described (Sambrook et al., 1989). General protocols for antibody-phage display technology are from the Pharmacia Biotech (Uppsala, Sweden) Recombinant Phage Antibody System (RPAS).
Construction of 508 scFv on the Phage Display:

The 508 IgM hybridoma used as the source for antibody variable-region sequences was generated from splenocytes of a mouse that had been immunized with a peptide corresponding to the 16 amino terminal residues of βAP conjugated to keyhole limpet hemocyanin, used as a carrier. mRNA extraction, first strand cDNA synthesis, PCR amplification of variable heavy ($V_H$) and variable light ($V_L$) sequences, and assembly of scFv cassettes, were done according to protocols essentially as described (Pharmacia Biotech RPAS manual). Assembled 508 scFv DNA was digested with SfiI and NotI, and 100 ng were ligated with 150 ng of vector DNA prepared by digestion of phagemid pCC-Gal6(Fv) (Berdichevsky Y et al., J Immunol Methods., 31;228(1–2):151–62, 1999) with SfiI and NotI. This phage-display system is designed to express the scFv in frame fusion protein with cellulose binding domain (CBD) derived from *Clostridium thermocellum* (Morag E et al. Appl Environ Microbiol., 61(5):1980–6, 1995). Ligated DNA was introduced into XL-1 Blue cells (Stratagene, La Jolla, Calif.) by transformation and transformants were plated onto 2 X YT Agar plates containing 100 μg/ml ampicillin and 1% glucose for overnight growth at 37° C.
Selection of β-amyloid Binding scFv-CBD Fusion Proteins:

Individual clones were picked and grown, each in 5 ml 2 X YT, 1% glucose, 100 μg/ml Ampicillin overnight at 30° C. IPTG was added at 1 mM for a 3 hr induction period. Soluble scFv-CBD fusion proteins were isolated from each clone by sonication of induced cell pellets. In order to identify functional soluble 508(Fv) from non-functional ones, 250 ng/well β-amhyloid peptide were covalently bound to epoxy-coated microtiter plates for 16 hr at 4° C. (Solomon, B., et al, Proc. Natl. Acad. Sci. USA., 93:452–455, 1996). The plates were washed with PBS/0.05%-Tween 20 (PBST), and blocked with a mixture of 3% bovine serum albumin and milk powder in PBS for 16 hr at 4° C. The plates were then washed and incubated with the soluble scFv-CBD recovered from the clones for 1 hr at 37° C. The bound antibody was detected with a rabbit anti CBD antiserum followed by HRP-conjugated goat anti rabbit antibodies. Plates were developed with the peroxidase chromogenic substrate ABTS and the signal was recorded with an ELISA microtiter plate reader at 405 nm. Positive phage clones (pCC-508(Fv)) were propagated and their DNA was sequenced using an automated model 373A DNA sequencer (Applied Biosystems, USA).
Production of 508(Fv)-CBD Fusion Proteins in *E. coli*:

For high level expression in *E. coli*, wild type (wt) and mutated 508(Fv) derivatives were cloned into the pFEKCA3 vector as described (Berdichevsky Y et al, Protein Expr Purif., 17(2):249–59, 1999). This lo vector utilizes the strong T7 promoter for expression, where the T7 RNA polymerase gene is carried as a lac repressor controlled-IPTG inducible gene in *E. coli* BL21 (DE3) (Studier, F. W., et al., Methods Enzymol., 85, 60–89, 1990). Upon IPTG induction, 508(Fv)-CBD proteins accumulated as insoluble inclusion bodies. They were recovered by the cellulose-assisted refolding method as previously described (Berdichevsky Y et al, Protein Expr Purif., 17(2):249–59, 1999). SDS polyacrylamide gel electrophoresis (SDS/βAGE) was used to separate proteins according to their molecular weight under denaturing conditions (Laemmli, U.K., Nature 227:263–270,1970).
Stability Assay of the Purified 508(Fv)-CBD Protein:

The activity of purified 508(Fv)-CBD protein was checked before and after storage at 4° C. for 7 days. 250 ng/well β-amyloid peptide was covalently bound to epoxy-coated wells of microtiter plates for 16 hr at 4° C. (Solomon B. et al., Proc. Natl. Acad. Sci. USA. 94, 4109–41 12, 1997). Wells were blocked with a mixture of 3% bovine serum albumin and bovine hemoglobin in PBS for 2 hr at 37° C., then washed and incubated with the 508(Fv)-CBD protein (0.5 μg/ml or as otherwise specified) for 1 hr at 37° C. Bound antibody fragments were detected by incubation with HRP-conjugated rabbit anti-mouse antibodies (BioMakor, Rehovot, Israel), diluted 1:5,000 and rabbit anti CBD diluted 1:10,000 in PBST for 1 hr at 37° C. The bound antibody fragments were monitored as described above.
Construction of a Phage Library for the Isolation the 508(Fv) βAP Binding Mutants:

Splicing overlap extension (SOE) PCR technique (Lefenbrve. B., et al., Biotechniques, 19:186–188, 1995) was used to replace $V_L$ cysteine codon 96 of 508(Fv) with other codons. pCC-508(Fv) DNA was used as template. In a first step, the template DNA was amplified with the following primers:

The antisense primer 508-mut-FOR: 5'-CCCCCCTCCGAACGTSNATGGGTAACT catcgCTGATGGCAGTA-3' (SEQ ID NO:10) inserts a PvuI restriction site (underlined), where S represents nucleotides C or G and N represents A, C, T or G. This primer was used for the replacement of cysteine codon 96 with phenylalanine (F), leucine (L), serine (S), tyrosine (Y) or tryptophan codons. The primer SfiI 5'BACK: 5'-ATCTATGC ggcccagccggccATG-3' (SEQ ID NO:11) inserts an SfiI site at the 5' end of the scFv. The resulting PCR product (SfiI-508mut) corresponds to the 5' half of 508(Fv)-CBD. In the second PCR step, the complete 508(Fv)-CBD was re-assembled by amplifying pCC-508(Fv) DNA with the SfiI-508mut PCR product from step 1 serving as the 5' end primer and CBD(BX): 5'-GTGGTGCTGAGTggatcctaTACTACACTGCCACCGGG-3' (SEQ ID NO:12) as the 3' end primer. The final PCR product (SfiI-508mut-BX) is a complete 508(Fv)-CBD cassette with replacements at $V_L$ codon 96 and an engineered PvuI restriction site as a silent mutation for analysis. SfiI-508mut-BX DNA was digested with SfiI, PvuI and NotI and ligated in a three fragment ligation with SfiI and NotI linearized pCC-Gal6(Fv) DNA which is a phagemid vector used to display an anti E. coli β-galactosidase scFv (Berdichevsky Y et al, J Immunol Methods., 3 1;228(1–2):151–62, 1999). The resulting ligated phagemid DNA was introduced into E. coli XL-1-Blue cells by electroporation. Cultures of E. coli were used to produce displaying phage by rescue with M13KO7 helper phage (Pharmacia Biotech, Uppsala, Sweden).

Affinity Selection of Fiamyloid Binding 508mut-(Fv) Displaying Phage Clones:

A sample containing rescued phage particles was subjected to one round of affinity selection (biopanning) and amplification; For the selection cycle, 0.5 μg/ml biotinylated β-amhyloid 1–16 amino acid peptide (βAP(1–16), acids 1–16 OF SEQ ID NO:3) in a total volume of 1 ml were used. The phages were pre-incubated with the biotinylated peptide for 2 hr at room temperature, and the reaction mixture was then layered on streptavidin-coated 30 mm polystyrene Petri dishes and incubated for 20 min at room temperature. Unbound phages were removed by extensive washing with PBST. The bound phages were eluted with 0.3 ml of 0.1 M HCl titrated to pH 2.2 with glycine. The eluate was neutralized with 80 pl of 0.5 M Tris (HCI) pH 10, and used to infect E. coli XL-1-Blue cells. Individual bacterial colonies containing amplified phage particles were used as a template for colony PCR (Novagen Madison, USA) with primers SfiI5'Back and CBD(BX). The PCR product of about the size of an intact scFv-CBD fragment (about 1250 bp) was digested with the restriction enzyme PvuI and analyzed by agarose gel electrophoresis.

ScFv Binding to Biotinylated βAP(1–16):

Binding of scFv to βAP(1–16) was analyzed by ELISA. Coated plates with 50 μl of 1 μg/ml streptavidin in 0.1 M NaHCO$_3$, pH 9.6, were washed three times with PBST and 50 μl of 6 ng/μl biotinylated βAP(1–16) were then added to the wells and incubated for 30 min at 37° C. Wells were blocked with a mixture of 3% bovine serum albumin and bovine hemoglobin in PBS for 2 hr at 37° C., then washed and incubated with the scFv (0.5 μg/ml or as otherwise specified) for 1 hr at 37° C. For inhibition experiments, peptides were pre-incubated with the antibody for 30 min at 37° C. before their addition to peptide coated wells. After washing, bound antibody fragments were detected as described above. βAP specific binding phage clones were propagated and their DNA was isolated and sequenced as described above.

Cell Culture and Cytotoxicity Assay:

Rat phenochromocytoma PC12 cells were cultured in DMEM supplemented with 5% horse serum, 10% fetal calf serum, 2 mM L-glutamine, and 100 units/ml penicillin/streptomycin and incubated at 37° C. under 5% CO$_2$. For the neurotoxicity assay, cultured PC12 cells were seeded into a 96-well plate at a density of $10^4$ cells/100 μl/well in a serum-free medium supplemented with 2 M of insulin. The effect on the prevention of the neurotoxicity of βA was measured as follows: 0.12 mM β-amyloid that was incubated for a week at 37° C. for the generation of fibrils, and further incubated in the presence of 508F(Fv)-CBD or with the unrelated Gal6(Fv)-CBD at a molar ratio of βAP to scFv of 15:1 or 30:1 for 24 hr. The βA/antibody mixture was added to the wells containing PC12 cells. The plates were incubated at 37° C. for 2 days, after which cell viability was assessed by measuring cellular redox activity with 3-(4,5-dimethylthiazol-2-yl)-2,5-diphenyl tetrazolium bromide (MTT), as described (Sladowski, D. et al., J. Immunol. Methods., 157:203–207,1993). The plates were incubated overnight at 37° C. MTT reduction was determined calorimetrically using an ELISA microtiter plate reader set at 550 nm.

Thioflavin T(ThT) Fluorimetry:

Aggregation of β-amhyloid peptide was measured by the Thioflavin T (ThT) binding assay, in which the fluorescence intensity reflects the degree of β-amhyloid fibril formation. ThT characteristically stains amyloid-like deposits (Levine, H. III, Protein Sci., 2: 404–410,1993) and exhibits enhanced fluorescence emission at 485 nm upon excitation at 435 nm when added to the suspension of aggregated β-sheet preparations. Aqueous solutions of 0.12 mM βAP in 0.1 M Tris (HCI) pH 7.1 were incubated at 37° C. for 1 week and further incubated in the presence of 508F(Fv)-CBD or with the unrelated Gal6(Fv)-CBD at a molar ratio of βAP to scFv of 15:1 or 30:1 for 24 hr. The fluorescence was measured after addition of 1 ml of ThT (2 MM in 50 mM Glycine, pH 9) with an LSB-50 Perkin Elmer Ltd., UK, spectrofluorimeter.

Preparations of Phage Delivery System:

12 Balb/c-female mice were divided to four groups of 3 mice per group. One group was used as control. Following a single dose of $10^{11}$ phage particles (fd phage, taken from a 15-mer phage peptide library which was provided by George P. Smith, University of Missouri, Columbia, Mo.) administered intranasally, mice were sacrificed in intervals of 1, 14 and 28 days in each group and their brains were taken for further analysis.

Ability of Phage Carrying scFv to Enter/remove βAP Fragment from the Brain:

ScFv-508F fusion to filamentous minor coat gpIII were used in order to investigate the ability of βAP anti-aggregating scFv to be carries by a filamentous phage display system directly into the CNS.

This scFv was prepared from anti-aggregation hybridoma 508 as described above and preserved its specific binding activity. Nine Balb/c mice divided into three groups were treated as follows: Mice of a first group were treated with 0.2 ml of $10^{-3}$ M biotin βA(1–16) alone. Mice of a second group were treated with a mix of $10^{10}$ phage carrying 508F-scFv which were pre incubated with 0.2 ml of $10^{-3}$ M biotin βA(1–16) for 1 hr. Mice of a third group were used as control. Following a single dose applied intranasally, mice were sacrificed in each group in intervals of 1, 14 and 28 days and their brains were taken for further analysis.

Preparations of Tissue Sections:

Immediately following decapitation, brains were removed and cut into two halves along the mid-sagittal sinus. Randomly, one half-brain was fixed by immersion in 4% paraformaldehyde solution in 0.1 M phosphate buffer for two hours in 4° C. and then immersed for cold protection in 4.5% sucrose in 0.1 M PBS over night. The sections were then moved to 30% sucrose for 2 hr in 4° C. Sections of coronal blocks containing the olfactory and hippocampus were put in OCT and cut with thick-nesses of 6 μm with a cryostat at −20° C., and then taken up on glass slides. Slides were kept at −70° C. These slides were used for phage detection using an immunofluorescence technique.

The other mid-sagittal half-brain was used for preparing paraffin tissue section for histology. The section were fixed in 4% paraformaldehyde for 2 hr, then transferred to 10% formalin saline for 2 days in room temperature, followed by embedding in paraffin, and cut with thick-nesses of 4 μm on a microtom and then taken up on glass slides. The slides were kept at room temperature until used.

Detection of Antigen in Brain Sections:

Immunofluorescence: Sections were blocked with 3% bovine serum albumin in PBS for 30 min and then incubated with rabbit polyclonal serum anti fd (1:100) or Streptavidin coupled with PE (sigma) for 1 hr at 37° C. Slides were then washed three times, 5 min each, in PBS, treated again with the blocking buffer for 5 minutes at room temperature, and then reacted with secondary r Cy™ 3 donkey anti-rabbit IgG (for phage detection) at 1:400 (sigma) or with streptavidin coupled to PE, 1:50 dilution, for 1 hr at room temperature. Finally, the preparations were washed three times in PBS, observed using a fluorescence microscope at a final magnification of ×10, and recorded on film or using a Hamamatsu digital camera (C4742) and Metamorph (Universal Imaging; West Chester, Pa.) computer software.

Histology: Six-micrometer sections were stained with hematoxylin and eosin. The stained sections were examined and photographed at a final magnification of ×40. Finally, the preparations were washed three times in PBS, observed on a microscope, and recorded on film.

Immunization with f13-YYEFRH:

Immunizations were performed with a genetically engineered fd phage carrying the peptide YYEFRH (SEQ ID NO:7) fused to its minor coat gpIII. Doses of $10^{10}$ phages per injection were used to immunize at 14-day intervals, through intraperitoneal injections. Mice were injected the phages with or without Freund's complete adjuvant (Difco) for the first injection and Freund's incomplete adjuvant (Difco) for the second injection. Following 7 days of each injections, the mice were bled and their serum were tested by ELISA for antibody IgG reactivity for both phage coat proteins and for βA.

Epitope Libraries:

The 15-mer phage-peptide library used in this study was provided by George P. Smith (University of Missouri, Columbia, Mo.). The library consists of about $1.9 \times 10^9$ phage particles and comprises a random peptide repertoire of 15 amino acid residues fused to coat glycoprotein VIII of the fd phage. Experiments with this library were carried out according to instructions of the provider (George P. Smith University of Missouri, Columbia, Mo.).

Biotinylation of Antibodies:

For antibody biotinylation, 100 μg of each antibody in 0.1 M NaHCO$_3$, pH 8.6, was incubated for 2 hr at room temperature with 5 μg of biotinamidocoproate N-hydroxysuccinimide ester (Sigma, B 2643) from a stock solution of 1 mg/ml in dimethylformamide and dialyzed at 4° C. against phosphate-buffered saline (PBS; 0.14M NaCl/ 0.01 M phosphate buffer, pH 7.4) overnight.

Isolation of Phage Presenting Epitopes from Peptide Library:

A library sample containing $10^9$ infectious phage particles was subjected to three rounds of selection (biopanning) and amplification. For each selection cycle a biotinylated monoclonal antibody (1 μg/μl) in a total volume of 25 μl was used. The phage clones were pre incubated with the biotinylated antibody overnight at 4° C., and the reaction mixtures were then layered in 1 ml of PBS containing 0.5% Tween 20 on streptavidin-coated 30 mm polystyrene Petri dishes and incubated for 20 min at room temperature. Unbound phages were removed by extensive washing (10 times for 10 min each) in PBS/0.05% Tween 20. The bound phages were eluted with 0.3 ml of 0.1 M HCl titrated to pH 2.2 with glycine. The eluate was neutralized and used to infect *E. coli* K91 cells. After three rounds of panning individual bacterial colonies containing amplified particles were grown on a microtiter plate and the selected phages were tested by ELISA for their ability to bind to the studied antibody, as described below.

Antibody Binding to Isolated Phage:

Binding of antibodies to phage was analyzed by ELISA. Wells of microtiter plates (Maxisorb, Nunc) were coated with 50 μl (at dilution of 1:1000 in 0.1 M NaHCO$_3$, pH 8.6) of rabbit anti-phage serum and incubated overnight at 4° C. The wells were blocked with a mixture of 3% bovine serum albumin and hemoglobin at a ratio of 1:1 (in PBS) for 2 hr at 37° C. Coated plates were washed three times with PBS/0.05% Tween 20, and 50 μl of enriched phage clones containing $10^{10}$ phage particles were added to the wells and incubated for 1 hr at 37° C. After washing, the studied antibody was added (1 μg/ml or as otherwise specified) and allowed to bind to the coated plate overnight at 4° C. and the binding constant thereof was measured. Positive phage clones were propagated and their DNA were sequenced in the insert region at the Sequencing Unit of the Weizmann Institute of Science (Rehovot, Israel) by using Applied Biosystem Kit (United States, Applied Biosystem).

fd gpVIII Phage Display off βA(1–16):

Coat glycoprotein VIII of filamentous phage is presented in approximately 2700 copies on the phage coat. The following oligonucleotides were prepared: sense—5'-agctccGATGCTGAATTCGGTGATAGCGGCTACGAAGT GCATCATCAGAAAcctgcag-3' (SEQ ID NO:13); and antisense—5'-ggTTTCTGATGATGCACTTC GTAGCCGCTATCATGACGAAATTCAGCATCgg-3' (SEQ ID NO: 14). These oligonucleotides were used to form a duplex (68–70° C., 10 minutes, followed by slow cool to room temperature) which encodes for amino acids 1–16 of human βAP and contain a silent mutation of a specific restriction site (EcoRI) which is useful for further analysis. The duplex was phosphorylated and lygated into HindlII/ PstI linearized f88-4 phagemid, which is a vector used to display fusion peptides on gpVIII of filamentous phage. The resulting ligated phagemid DNA was introduce into *E. coli* K91K cells by transformation and transformants were plated onto 2×YT Agar plates containing 10 μg/ml tetracycline and 1% glucose for overnight growth at 37° C. Individual bacterial colonies containing phage particles were used to inoculate 2YT medium containing. 10 μg/ml tetracycline for overnight growth at 37° C. for amplification. The DNA phagemid product obtained from each colony was analyzed by EcoRI. Positive clones were further amplified for antigen preparation.

Immunization with f88-EFRH:

Immunizations were performed with a genetically engineered fd phage carrying the peptide V$_H$EPHEFRHVAL-NPV (SEQ ID NO:8) fused to its major coat glycoprotein VIII. Doses of $10^{10}$ phages per injection were used to immunize at 14-day intervals, through intraperitoneal injections. Mice were injected the phages with or without Freund's complete adjuvant (Difco) for the first injection and Freund's incomplete adjuvant (Difco) for the second injection. Following 7 days of each injections, the mice were bled and their serum were tested by ELISA for antibody IgG reactivity for both phage coat proteins and for βA.

Inhibition of Antibody Binding to β-amyloidpeptide:

The inhibition of antibody binding to βAP(1–16) by various small peptides was performed using 250 ng/well biotinylated β-amhyloid peptides (1–16) bound covalently to ELISA plates as previously described. The plates were washed with PBS/0.05% Tween 20 and blocked with a mixture of 3% bovine serum albumin and hemoglobin, ratio 1:1 (in PBS) for 2 hr at 37° C. The peptides were pre incubated with 1:3000 dilution of serum after third immunization with f88-EFRH for 30 min at 37° C. before their addition to βAP-coated wells and were left overnight at 4° C. therein. After washing, bound antibody was detected by incubation with HRP-conjugated rabbit anti-mouse immunoglobulin, as described above. The results were used to derive the IC$_{50}$, which is the half molar concentration of peptide that fully inhibits antibody binding. Peptides were synthesis by Applied Biosystems Synergy Model 430A in the Unit for Chemical Services of The Weizmann Institute of Science by solid-phase using Fmoc chemistry.

Cell Culture and Cytotoxicity Assay:

Rat phenochromocytoma PC12 cells were cultured in DMEM supplemented with 5% horse serum, 10% fetal calf serum, 2 mM L-glutamine, and 100 units/ml penicillin/ streptomycin and incubated at 37° C. under 5% $CO_2$. For the neurotoxicity assay, cultured PC12 cells were seeded into a 96-well plate at a density of $10^4$ cells/100 μl/well in a serum-free medium supplemented with 2 M of insulin. The effect on the prevention of the neurotoxicity of βA was measured as follows: 0.12 mM β-amyloid that was incubated for a week at 37° C. for the generation of fibrils, and further incubated in the presence of serum of EFRH-phage immunized mice and serum of a non-relevant phage immunized mice at dilutions of 5:1 and 10:1 for 24 hr. The βA antibody mixture was added to the wells containing PC12 cells. The plates were incubated at 37° C. for 2 days, after which cell viability was assessed by measuring cellular redox activity with 3-(4,5-dimethylthiazol-2-yl)-2,5-diphenyl tetrazolium bromide (MTT), as described (Sladowski, D. et al., J. Immunol. Methods., 157:203–207, 1993). The plates were incubated overnight at 37° C. MTT reduction was determined colorimetrically using an ELISA microtiter plate reader set at 550 nm.

EXPERIMENTAL RESULTS

Examples 1–6 below relate to the production of a single chain version of the anti aggregating monoclonal antibody. Examples 7–8 below relate to delivery of peptide or antibody displaying phage to the brain. Examples 9–14 below relate to the production of high titers of anti-aggregating polyclonal antibodies by direct immunization with beta amyloid antigens displayed on a phage, and to characterization of these antibodies.

Example 1

Generation of an IgM Hybridoma 508

Immunization of a mouse with a 16 amino acid peptide of beta-amnyloid (acids 1–16 of SEQ ID NO:3) conjugated to KLH (SEQ ID NO:9) was carried out as described hereinabove. Repetitious immunization eventually produced a low but measurable antibody titer against beta-amyloid. Subsequent splenectomy of the immunized mouse facilitated preparation of IgM hybridoma 508 expressing scFvAb with specificity to beta-amyloid. RNA was subsequently extracted from this hybridoma. The IgM 508 hybridoma showed specific activity to Aβ in preventing its toxic affects on PC12 cells (Anavi, S. 1998, M. Sc. thesis from the department of Molecular Microbiology and Biotechnology of the Tel-Aviv University, I).

Example 2

Cloning of the Variable Domains of the 508 IgM Hybridoma as a scFv

Figure 3:
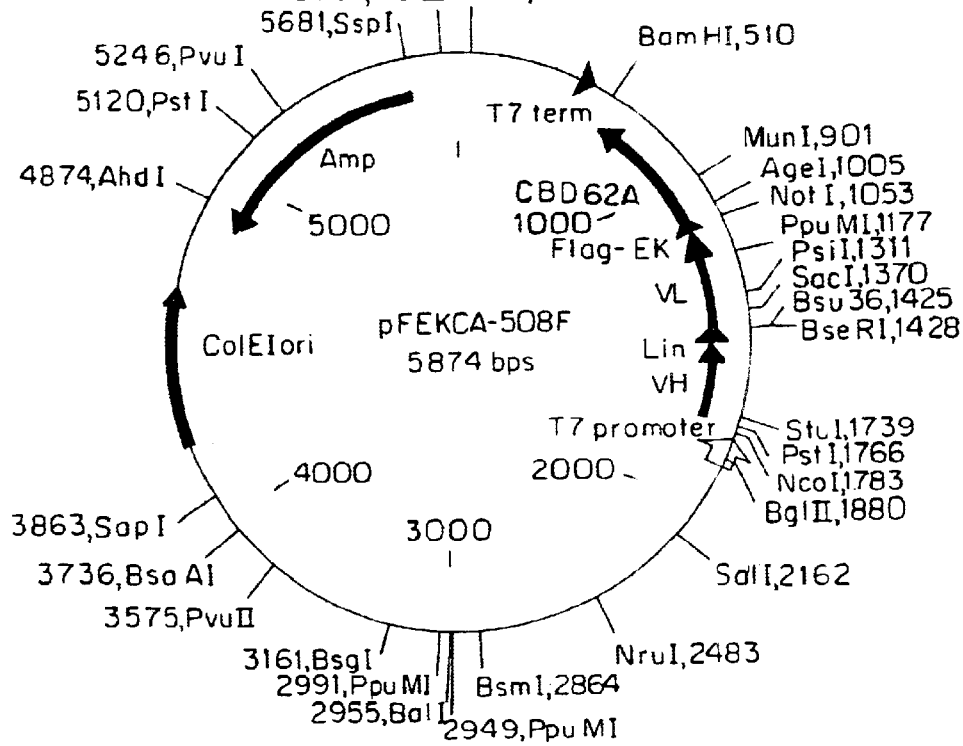
FIG. 3 is a physical map of plasmid pfFEKCA-508 which is used according to the present invention for cytoplasmic expression of the scFv-508-CBD fusion protein under the control of a $T_7$-promoter. Amp res—a gene encoding β-lactamase; $V_H$ and $V_L$—sequences coding for the variable domains of the heavy and light chains of scFv-508, respectively; Lin—a gene coding for a $(Gly_4Ser)_3$ (SEQ ID NO:2) linker present between the variable domains $V_H$ and $V_L$. T7-promoter and T7 term—T7 promoter and T7 terminator sequences, respectively. Restriction sites and positions thereof are also shown.
Figure 4:
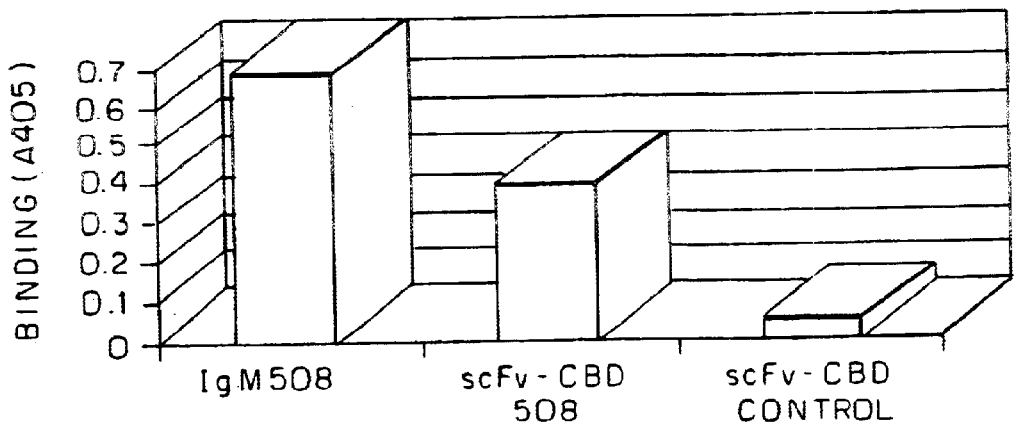
FIG. 4 shows an analysis of βAP binding by antibody 508(Fv)-CBD in an ELISA assay. The analyzed antibodies were added to βAP coated wells. Bound antibodies were detected with HRP conjugated secondary antibodies. The parental 508 IgM antibody was used as a positive control. The unrelated anti-β-galactosidase antibody Gal6(Fv)-CBD was used as a negative control.
Figure 5:
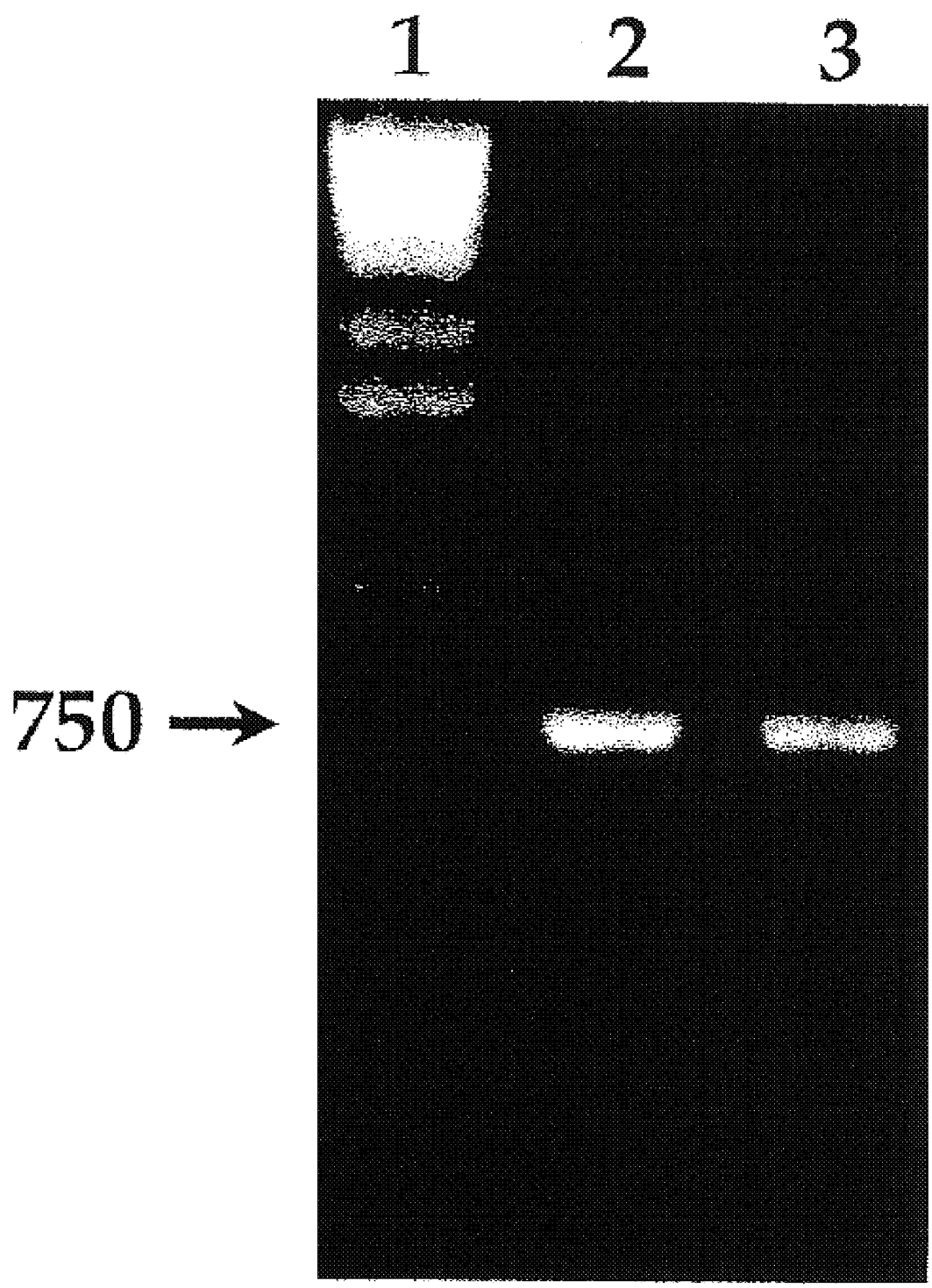
FIG. 5 shows PCR analysis of phage DNA inserts. DNA isolated from pCC-508(Fv), lane 2, and pCC-Gal6(Fv), Lane 3, were PCR amplified and separated on a 1.5% agarose gel. Ethidium bromide staining and UV illumination were used to visualize the bands. Lane 1 contains a DNA size marker. The arrow marks the position of an intact scFv migrating at about 750 bp.

MAb 508 showed specific recognition of β-amhyloid and prevented its toxic affects on PC 12 cells (Anavi S., 1998, ibid). For cloning the 508 antibody as a scFv in a phage display vector, RNA was extracted from $10^8$ 508 hybridoma cells and was used as a source for antibody variable region coding sequences. RT-PCR was used to amplify the variable domains that were cloned into the phage display vector pCC-Gal6(Fv), as described in Materials and Methods. When hybridoma derived antibodies are cloned as scFvs, some of the clones may contain aberrant sequences that are not functional. Therefore, to identify phagemid clones carrying functional β-amyloid binders from the generated clones, 10 individual clones were picked at random and soluble scFv-CBD fusion protein was produced thereby. FIG. 2 shows a physical map of plasmid pCC-508 which was used to express the 508-scFv. The CBD domain serves as an immunological detection of soluble scFv protein or as a novel approach in refolding of soluble scFv protein inclusion bodies of overexpressed protein (Berdichevsky Y et al, Protein Expr Purif., 17(2):249–59, 1999). The plasmid used for 508-scFv over expression is shown in FIG. 3. The soluble scFv-CBD from the selected clones was incubated in wells of an ELISA plate that has been coated with β-amyloid peptide. Of the analyzed clones, 50% showed specific binding to βAP. FIGS. 1a–e demonstrate and illustrate the preparation of 508 scFv from IgM antibody. FIG. 4 shows βAP binding by the scFv-CBD produced by a positive clone that was chosen for further analysis. PCR analysis. was used to characterize its DNA insert. It was found that the positive clone (designated pCC-508(Fv)) contained an intact DNA insert (FIG. 5). DNA sequencing of pCC-508(Fv) confirmed that the clone expresses an intact scFv fragment (see, FIGS. 11a–b and SEQ ID NOs:5 and 6, for nucleic and amino acid sequences, respectively, modified as further described below).

Example 3

Site Directed Mutagenesis of 508-(Fv) Antibody

Figure 7:
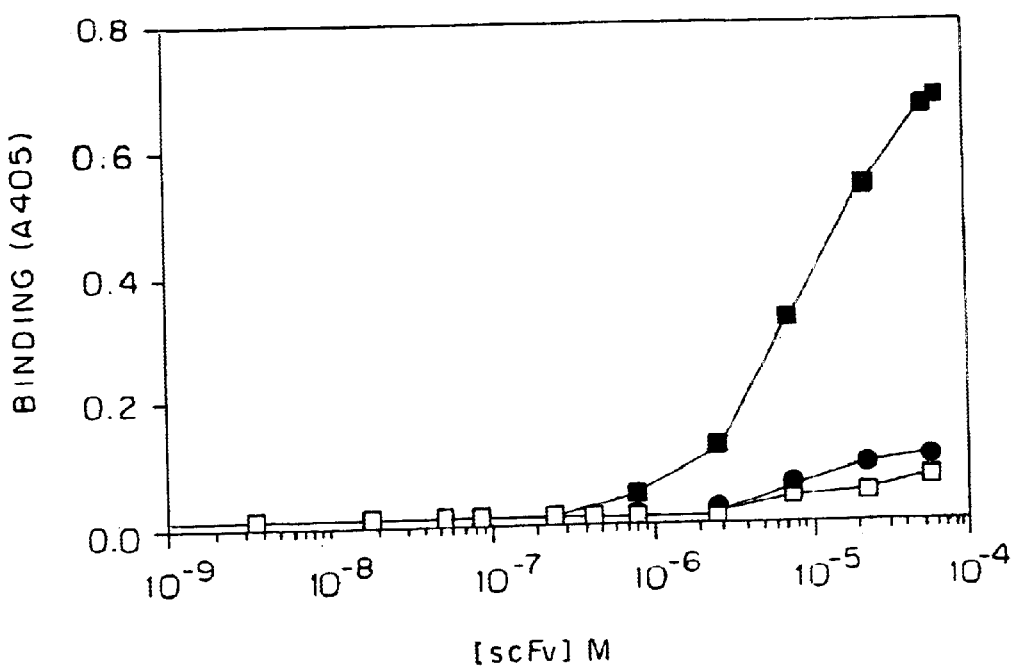
FIG. 7 demonstrates the stability of 508(Fv)-CBD. Purified 508(Fv)-CBD protein was stored at 4° C. for one day (dark squares) or one week (dark circles), and then analyzed for βAP binding in an ELISA assay, as described in the legend to FIG. 4. The unrelated antibody Gal6(Fv)-CBD served as a negative control (open squares).
Figure 6:
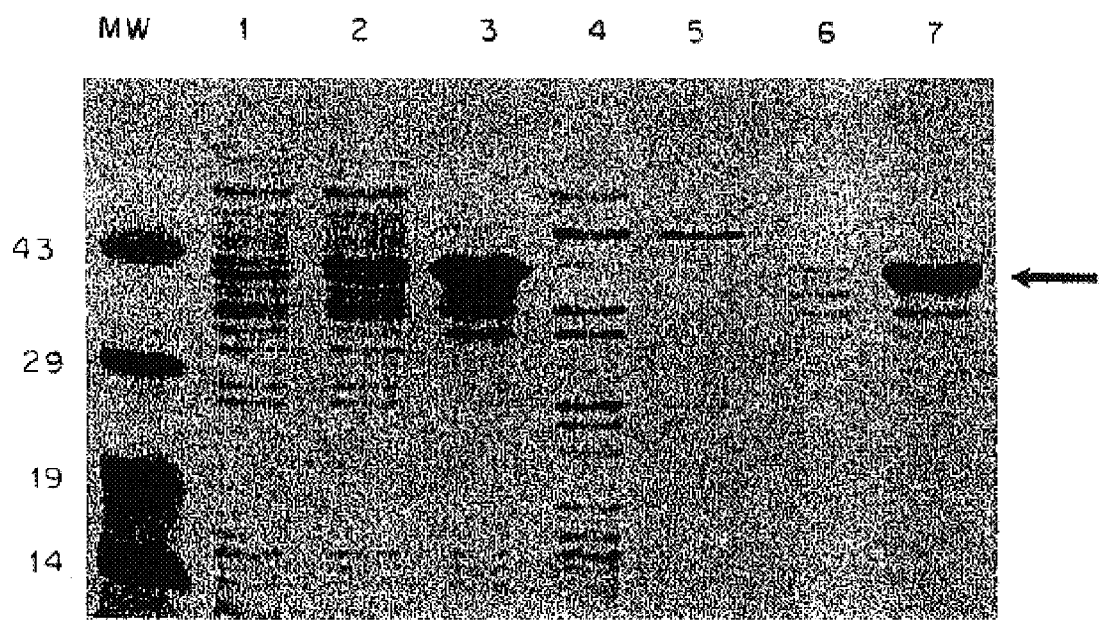
FIG. 6 demonstrates expression and purification of 508 (Fv)-CBD. 5–10 μg protein were loaded in each lane of a 14% SDS polyacrylamide gel. Proteins were visualized by Coomassie brilliant blue staining. The arrow marks the position of the scFv-CBD fusion protein. Lane 1—total cell extract from non-induced BL21(DE3) cells carrying 508 ((Fv)-CBD expression vector. Lane 2—total cell extract from BL21(DE3) cells carrying 508((Fv)-CBD expression vector induced for 3 hours with IPTG. Lane 3—washed, solubilized and reduced inclusion bodies that were used in refolding. Lane 4—protein that did not bind to cellulose during cellulose-assisted refolding. Lane 5—protein washed away from cellulose with TBS. Lane 6—protein washed away from crystalline cellulose with distilled water. Lane 7—soluble 508(Fv)-CBD recovered from cellulose by high-pH elution and neutralization.

The DNA sequencing analysis of pCC508-(Fv) revealed the unusual appearance of a cysteine residue at the position 96 of V$_L$ CDR3 (Kabat, E. A. et al., Sequences of proteins of immunological interest, 5th Ed., 1991). The deduced amino acid sequence of $V_L$ CDR3 is: $H^{89}QRSSYPCT^{97}$ (SEQ ID NO:15). The presence of an unpaired cysteine residue in a scFv may reduce its folding yield and also decrease its stability in solution and its storage half life. Therefore, 508(Fv) was subcloned into an expression vector and produced in *E. coli* as described in Materials and Methods. FIG. 6 summarizes the production process of 508(Fv)-CBD by the cellulose-assisted refolding method (Berdichevsky Y et al, Protein Expr Purif., 17(2):249–59, 1999). Although 508(Fv)-CBD could be purified to near homogeneity (FIG. 6 lane 7) by this method, it refolded relatively poorly and was unstable upon storage at 4° C. (FIG. 7). It was assumed that substitution of the cysteine with a different residue may increase the production yield and stability of the soluble scFv without having an adverse affect on its affinity (Kirpriyanov, M. S. et al., Protein Engineering, 10:445–453, 1997).

Figure 8A:
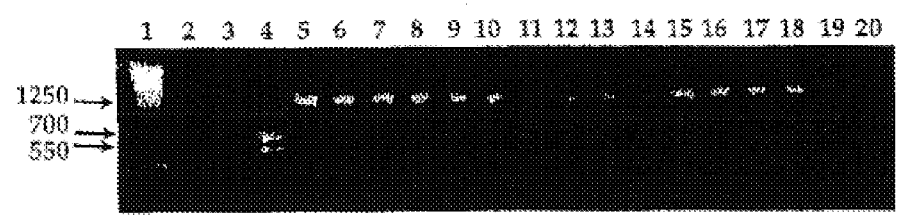
FIG. 8(*a–b*) demonstrates quantitation of 508(Fv) mutants affinity-enrichment by PCR and DNA restriction analysis. The DNA of 19 508(Fv)-mutant micro library clones before (FIG. 8*a*) and of 11 clones picked up after one cycle of affinity selection (FIG. 8*b*) were analyzed. The DNA was digested with PvuI and separated on a 1.5% agarose gel. A non-mutated scFv-CBD appears as an intact 1250 bp fragment (upper arrow). A mutated clone is indicated by the appearance of both 700 bp (middle arrow) and 550 bp (lower arrow) fragments. A DNA size marker is shown in lane 1.
Figure 8B:
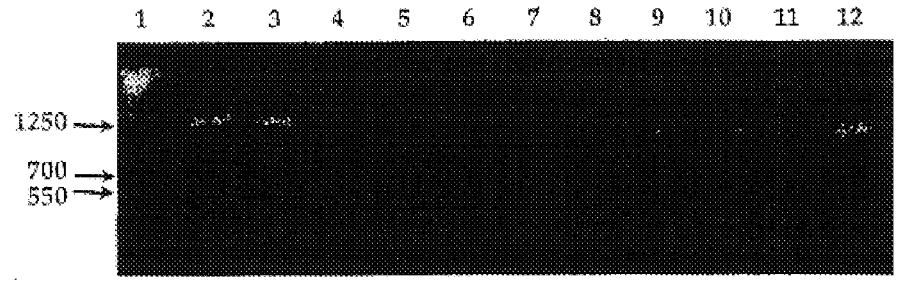

For the replacement of the 508 $V_L$ cysteine 96 codon SOE PCR was used, which enabled the replacement of Cys 96 with phenylalanine, leucine, serine, tyrosine or tryptophan codons. In addition, the PCR scheme employed permits the persistence of the cysteine residue at that position. 508(Fv) mutants were cloned into the pCC-Gal6(Fv) phage vector, resulting in the generation of a micro library (having 6 potential variant). The replacing residues chosen are generally acceptable at that CDR3 position, as they are found in various antibodies in the Kabat database (Kabat, E. A. et al., Sequences of proteins of immunological interest, 5th Ed., 1991). However, different replacements may vary in their effect on βAP binding. To test which replacement maintains βAP binding, a single cycle of affinity selection was performed on the 508(Fv)-Mut micro phage library using biotinylated βAP(1–16) as a capturing antigen. PCR amplification and restriction analysis was used to monitor the enrichment of library clones after the affinity selection cycle. When the 508Mut-(Fv)-CBD DNA is digested with PvuI, a typical restriction pattern is obtained upon agarose-gel electrophoresis and ethidium-bromide staining. The lower 750 and 500 bp fragments represent the 508Mut-(FV)-CBD DNA, while an intact 1250 bp fragment represent scFv-CBD from the pCC-Gal6(Fv) DNA which was used as a vector. It was found that before affinity selection the library was heavily contaminated with the pCC-Gal(Fv) vector DNA. This is evident from the fact that the DNA of 18/19 randomly picked library clones was not cleaved at the PvuI site engineered adjacent to 508 $V_L$ position 96. Only one of the 19 analyzed clones showed the expected restriction pattern associated with a mutation (FIG. 8a). However, after affinity selection, 5/11 randomly selected clones showed the expected restriction pattern (FIG. 8b). This indicates an enrichment factor of about 10 fold, which demonstrates the ability of 508 scFv mutants to bind the βAP(1–16) epitope. The DNA sequences of the 5 mutants were determined and shown in Table 1 below. Suitable replacements of 508 $L_L$ cysteine 96 codon were found to be phenylalanine, serine or tyrosine.

TABLE 1

| Lane (FIG. 8b) | Amino Acid Sequence | SEQ ID NO: |
|---|---|---|
| 4 | $^{89}$HQRSSYP-C$^{96}$-T | 16 |
| 5 | $^{89}$HQRSSYP-F$^{96}$-T | 17 |
| 6 | $^{89}$HQRSSYP-Y$^{96}$-T | 18 |
| 8 | $^{89}$HQRSSYP-F$^{96}$-T | 19 |
| 11 | $^{89}$HQRSSYP-S$^{96}$-T | 20 |

Example 4

The Recognition of βAP(1–16) by scFv 508 Mutants.

Figure 9A:
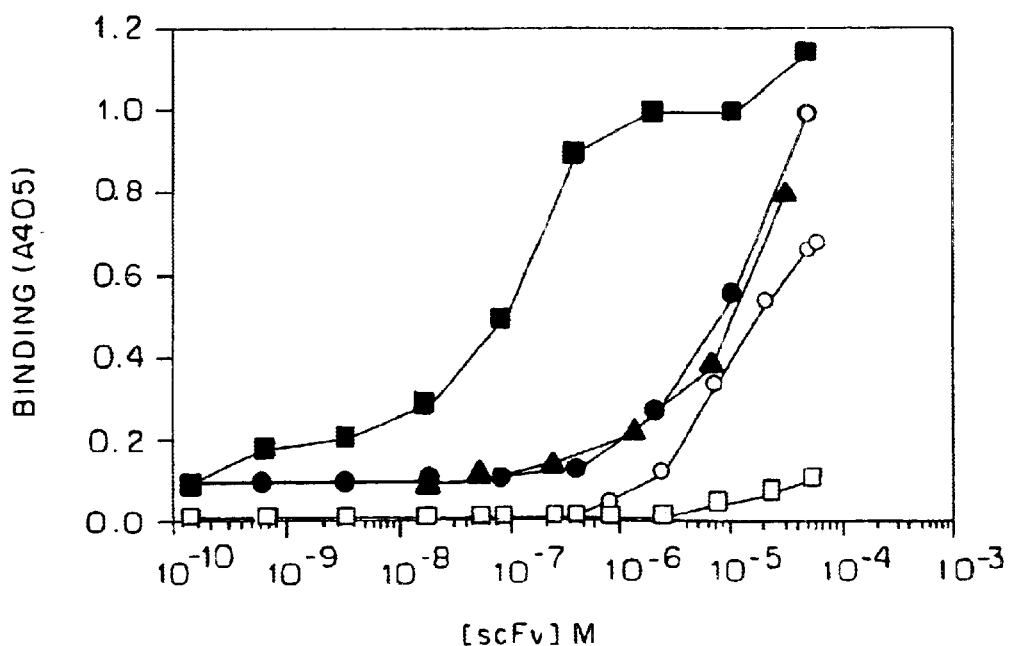
FIG. 9(*a–b*) shows an analysis of βAP binding (FIG. 9*a*) and stability (FIG. 9*b*) of mutated 508(Fv) derivatives in an ELISA assay. The analyzed antibodies were added to βAP coated wells. Bound antibodies stored at 4° C. for one day or for one week were detected as described in the legend to FIG. 7. 508(Fv) wild type (open squares), C96F (dark squares), C96Y (dark circles), C96S (dark triangles). The unrelated anti-β-galactosidase antibody Gal6(Fv)-CBD was used as a negative control (open squares).
Figure 9B:
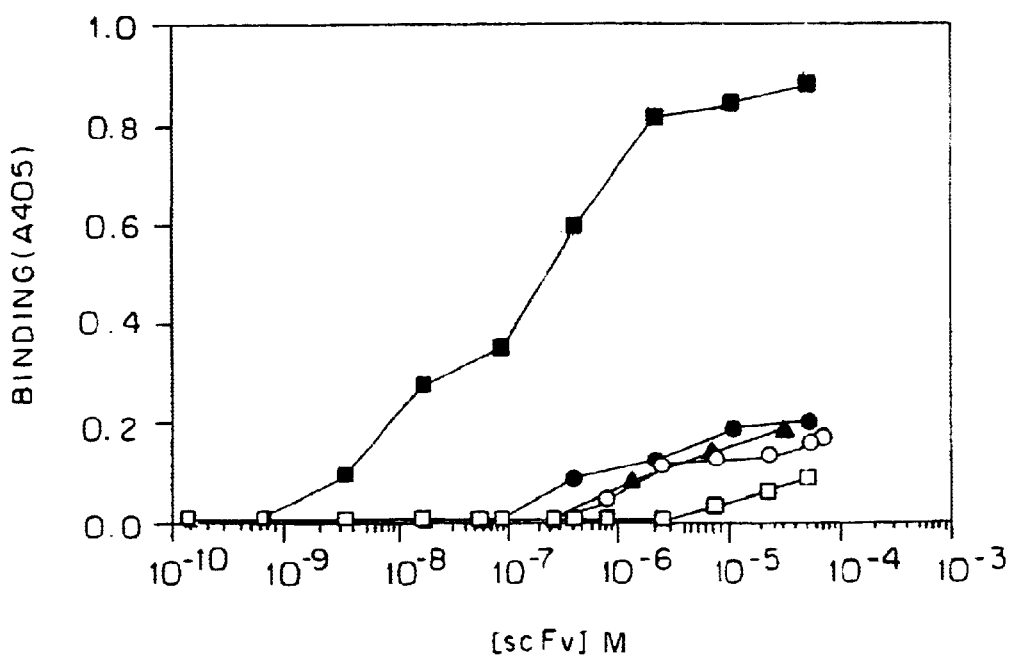
Figure 10:
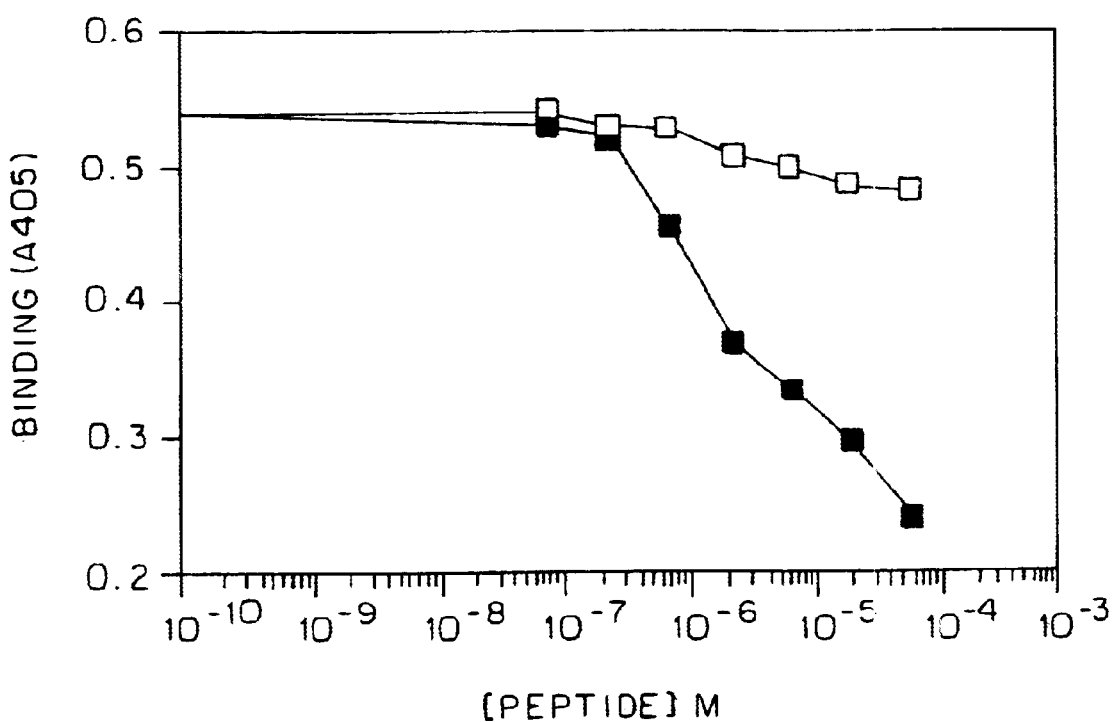
FIG. 10 shows an analysis of the specific inhibition of βAP binding by antibody 508F(Fv) in a competitive ELISA assay. The antibody was pre-incubated with varying concentrations of the competing peptides: βAP (acids 1–16 of SEQ ID NO:3) (dark squares) or the unrelated peptide WVLD (SEQ ID NO:4) (open squares), before being added to βAP coated wells. Bound antibodies were detected as described in the legend to FIG. 7.

For further examination of mutated 508 scFv derivatives, the muated genes were subcloned into an expression vector and overexpressed in *E. coli*, as described for the wild type protein above. The interactions of the various mutated 508-(Fv) proteins (Table 1) with βAP(1–16) were tested in an ELISA assay. FIGS. 9a–b show that while the wild type 508-(Fv)-CBD binds at a half maximum binding (HMB) of $10^{-5}$ M, all the mutants showed improved binding to βAP: the HMB of C96S and C96Y is $5 \times 10^{-6}$ M and the HMB of C96F is $10^{-7}$ M. For further examination the 508-scFv mutant that carries the C96F mutation (508F(Fv)) was chosen, which show the higher affinity and shelf stability FIGS. 9a–b). The specificity of βAP(1–16) binding by 508F(Fv) was tested in a competitive ELISA. As is shown in FIG. 10, binding of the purified 508F(Fv)-CBD to βAP was inhibited by soluble βAP(1–16) peptide serving as the competitor in the liquid phase in a dose-dependent manner. Inhibition of 50% binding was obtained at about 1 μM competitor. Binding was not affected by an irrelevant peptide (WVLD, SEQ ID NO:4).

Example 5

Prevention of the β-amyloid Neurotoxic Effect by 508F(Fv).

Figure 12:
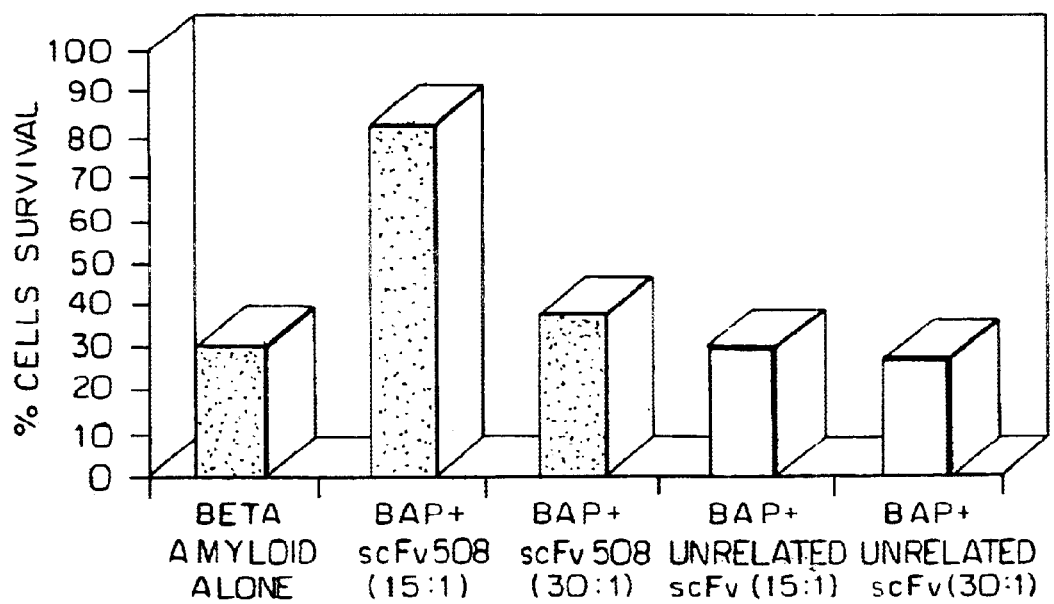
FIG. 12 demonstrates the prevention of βAP mediated toxic effect on PC12 cells by 508F(Fv). Cells were incubated with fibrillar βA alone, or with fibrillar βA that had been incubated with antibodies at different molar ratio of antibody/βAP, as indicated. An 3-(4,5-dimethylthiazol-2-yl)-2,5-diphenyl tetrazolium bromide (MTT) assay was used to estimate cell survival.

In order to find out whether 508F(Fv) exhibits a protective effect similar to the parental IgM antibody in preventing βA mediated neurotoxicity toward cultured cells, an in vitro test was applied using rat phenochromocytoma PC12 as described (Solomon B. et al., Proc. Natl. Acad. Sci. USA., 94: 4109–4112,1997). Viability of the cells exposed to βA with or without antibody was measured. As shown in FIG. 12, 508F(Fv) prevented the neurotoxicity of βA (90% cell viability) at a molar ratio βAP:scFv of 15:1, while the unrelated scFv showed no effect. Purified CBD or the scFv alone had no affect on the cells.

Example 6

Disaggregation of β-amyloid fibril by 508F(Fv)

Figure 13:
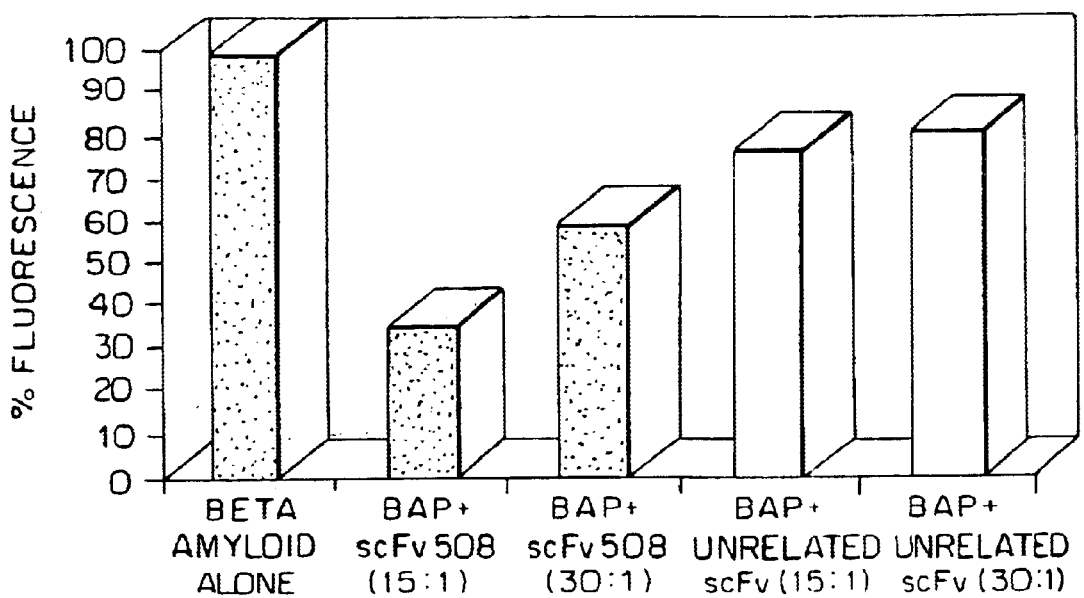
FIG. 13 demonstrates the disaggregation of fibrillar βA by 508F(Fv). The fibrillar state of pre-formed βA fibrils were measured with or without incubation with antibodies at different molar ratio of antibody/βAP, as indicated. The fluorescence of thioflavin-T (ThT) reagent in a ThT assay which is proportional to fibril βA was used to assess the fibril morphology.
Figure 14A:
FIGS. 14(*a–d*) demonstrate the detection of filamentous phage (f88-EFRH) in brain sections via immunofluorescence one day following a single dose applied intranasally. Appearance of filamentous phage in mouse olfactory bulb and hippocampus sections using fluorescent rabbit anti-phage antibody (FIGS. 14*a* and 14*c*, respectively) as is compare to an untreated mouse brain (FIGS. 14*b* and 14*d*, respectively). The is sections were observed using a fluorescence microscope at a final magnification of ×10.
Figure 14C:
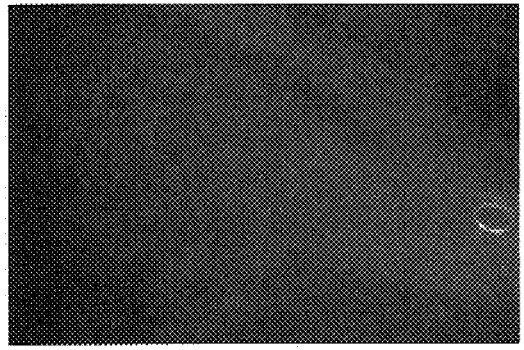
Figure 14B:
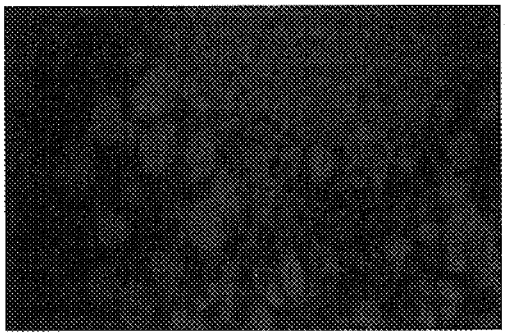
Figure 14D:
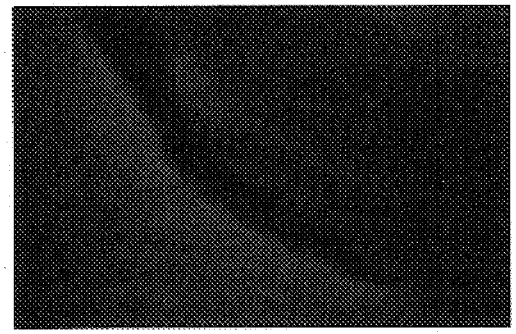
Figure 15A:
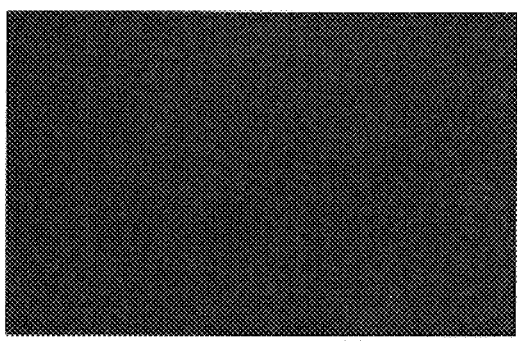
FIGS. 15(*a–d*) demonstrate the disappearance of filamentous phage (f88-EFRH) from mouse brain 28 days following a single intranasal administration. Disappearance of filamentous phage from mouse olfactory bulb and hippocampus is demonstrated in sections of these organs using fluorescent rabbit anti-phage antibody (FIGS. 15*a* and 15*c*, respectively), as is compared to an untreated mouse brain (FIGS. 15*b* and 15*d*, respectively). The sections were observed using a fluorescence microscope at a final magnification of ×10.
Figure 15C:
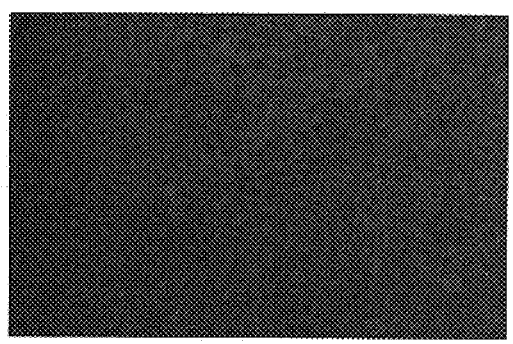
Figure 15B:
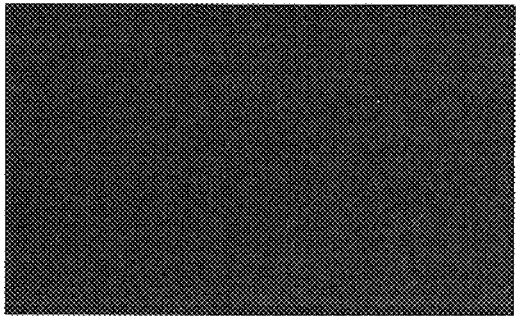
Figure 15D:
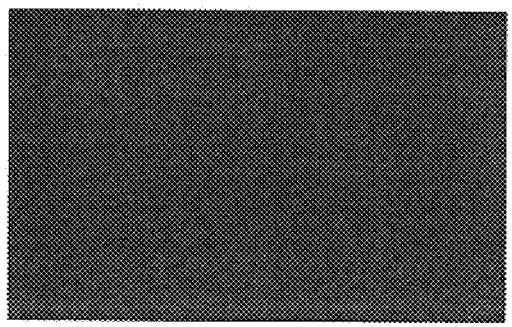
Figure 16A:
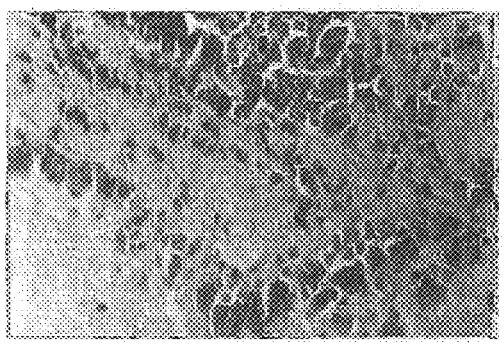
FIGS. 16(*a–d*) show histology of mouse brain sections after phage f88-EFRH clearance. Brain sections of olfactory organ (FIG. 16*a*) and hipocampous (FIG. 16*c*) after 28 days following phage f88g-EFRH administration were stained with hematoxylin and eosin, and compared to sections of an untreated brain (FIGS. 16*b* and 16*d*, respectively). The stained sections were examined and photographed at a final magnification of ×40.
Figure 16B:
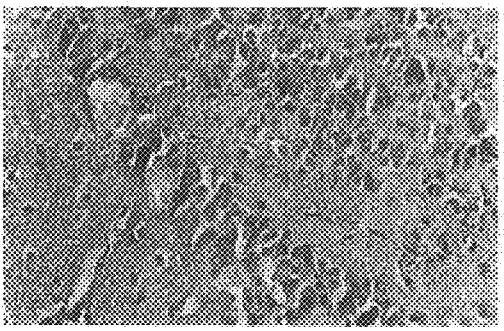
Figure 16C:
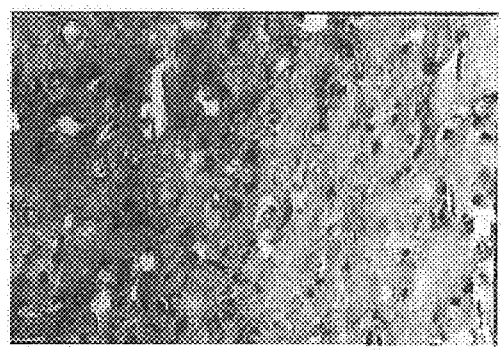
Figure 16D:
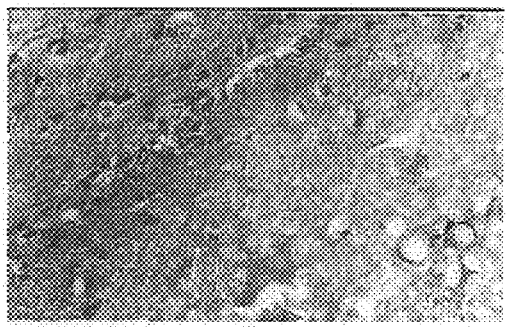
Figure 17A:
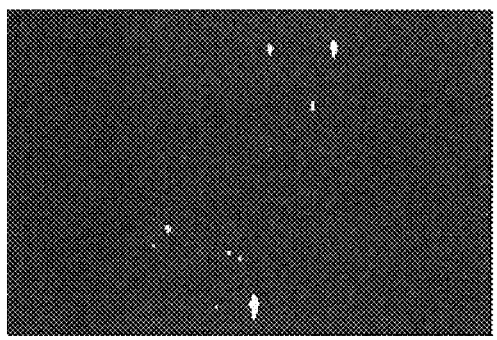
FIGS. 17(*a–d*) show fluorescence detection of biotin of phage pCC-508F coupled to biotinylated βAP (acids 1–16 of SEQ ID NO:3) in mouse brain sections following a single intranasal administration. Appearance of βAP (acids 1–16, SEQ ID NO:3) coupled to filamentous phage displaying scFv508F in mice olfactory bulb and hippocampus sections using streptavidin coupled to PE (FIGS. 17*a* and 17*c*, respectively) as is compare to an untreated mouse brain (FIGS. 17*b* and 17*d*, respectively). The sections were observed using a fluorescence microscope at a final agnification of ×20.
Figure 17C:
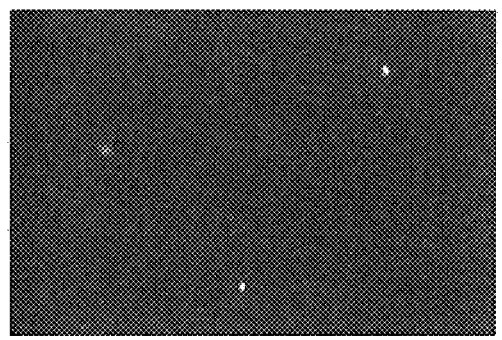
Figure 17B:
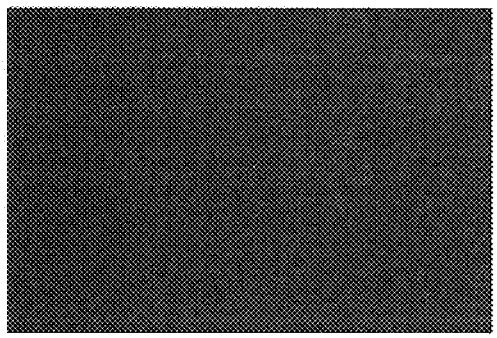
Figure 17D:
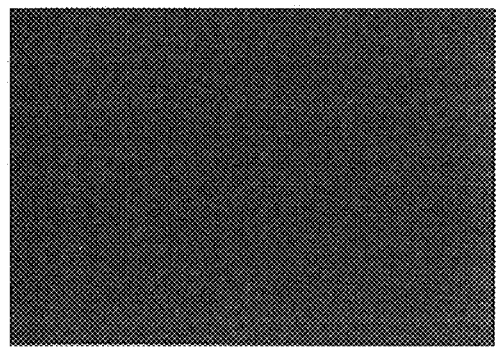
Figure 18A:
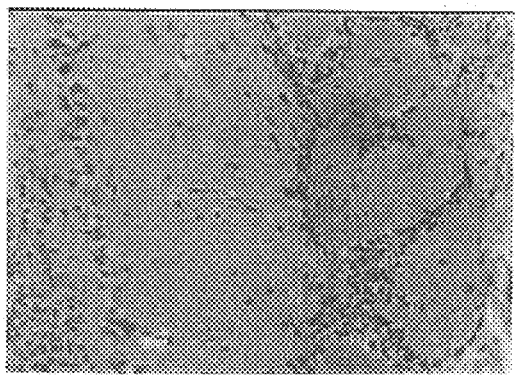
FIGS. 18(*a–d*) show histology of mouse brain after phage. pCC-508F coupled to biotinylated βAP (acids 1–16 of SEQ ID NO:3) administration. Olfactory organ (FIG. 18*a*) and hippocampus (FIG. 18*b*) sections one day following phage administration were stained with hematoxylin and eosin, and were compared to untreated mouse brain sections (FIGS. 18*c* and 18*d*, respectively). The stained sections were examined and photographed at a final magnification of ×40.
Figure 18C:
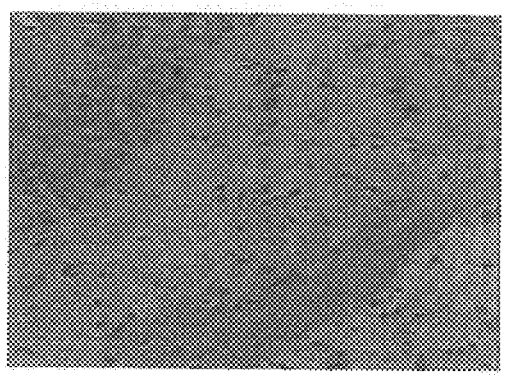
Figure 18B:
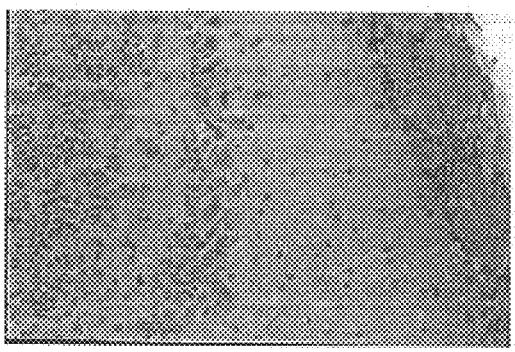
Figure 18D:
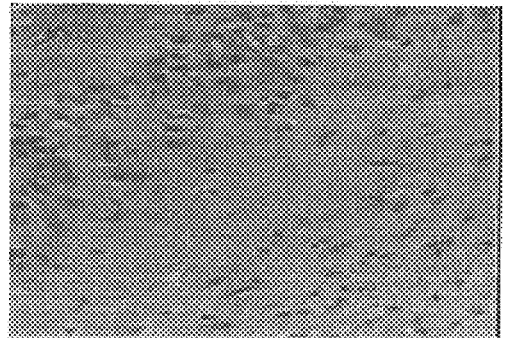

To examine the effect of 508F(Fv) on disruption of the βA fibril (the toxic form of βAP) the ThT reagent that binds specifically to fibrillar structures (Levine, H. III, Protein Sci., 2: 404–410,1993) was used. The interference with the already formed βA fibril was measured at the same molar ratio of βAP:scFv as in the βA neurotoxic assay and was quantitated by ThT fluorimetry. FIG. 13 shows that 508F (Fv) incubated with pre-formed βA fibrils disrupted the fibril structure indicating extensive deterioration of fibril morphology, as is evidenced by a substantial (62%) decrease in ThT fluorescence.

Example 7

Ability of Filamentous Phage to Enter the CNS via Olfactory Track

Female Balb/c mice were treated with phage vector f88-EFRH via intranasal administration. The propose of this experiment was to check the ability of filamentous phage to reach the hipocampous region via olfactory tract. Since the phage is not carrying any specific molecule for targeting neuron cells, it should be vanished without causing any harm after several day following the administration. In order to investigate the appearance of phage in the olfactory bulb and the hipocampous region double labeling of antibodies was used as follows: Rabbit polyclonal antibody anti filamentous phage and mouse monoclonal antibody against EFRH epitope fused to glycoprotein VIII of the phage surface. One day following a single intranasal administration of $10^{11}$ phages animals showed such phages in their olfactory bulb and hypocampous (FIGS. 14a–d). Seven days after the administration phages were detected in the olfactory bulb of only one mouse of the three tested, whereas no phages were revealed in the hypocampous. No evidence of phages was detectable 28 days following administration (FIGS. 15a–d). As shown in FIGS. 16a–d, no evidence of change in the neuron population of the brain of treated mice was evident.

Example 8

Filamentous Phage are Suitable Vehicle for Carrying Active Antibody Fragment to the CNS To check whether a filamentous phage can carry an antibody to the CNS via the olfactory track and still preserve the activity against β-amyloid a filamentous phage displaying 508F was incubated with $10^{-3}$ M biotinlated βAP(1–16), in order to form antibody antigen immunocomplex. Balb/c mice were divided into two groups and were administrated intranasally with two different antigens: 508F-βAP(1–16) immunocomplex and for comparison biotinlated βAP(1–16) alone. Following a single dose the mice were sacrificed and brain sections thereof prepared and reacted with streptavidin coupled to a fluorescent agent. Fluorescence was detected only in brain sections of mice that were administered with 508F-βAP(1–16), but not, or to a much lesser extent, in brain sections of mice that were administered with βAP (1–16) alone (FIGS. 17a–d). No hystological findings characterized treated mice io (FIGS. 18a–d).

It is therefore assumed that the phage act as an inert vehicle of antibody to the brain, carrying the βAP(1–16) molecule into the brain.

Example 9

Figure 19:
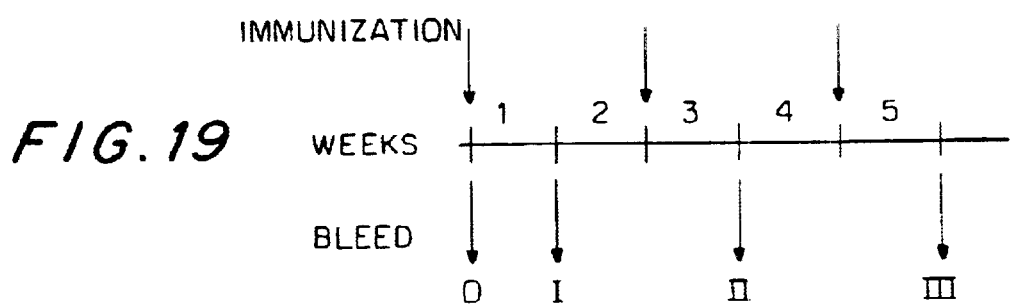
FIG. 19 is a diagram of immunization schedule with filamentous phage displaying the EFRH (SEQ ID NO:1) epitope of β-amhyloid peptide.
Figure 20A:
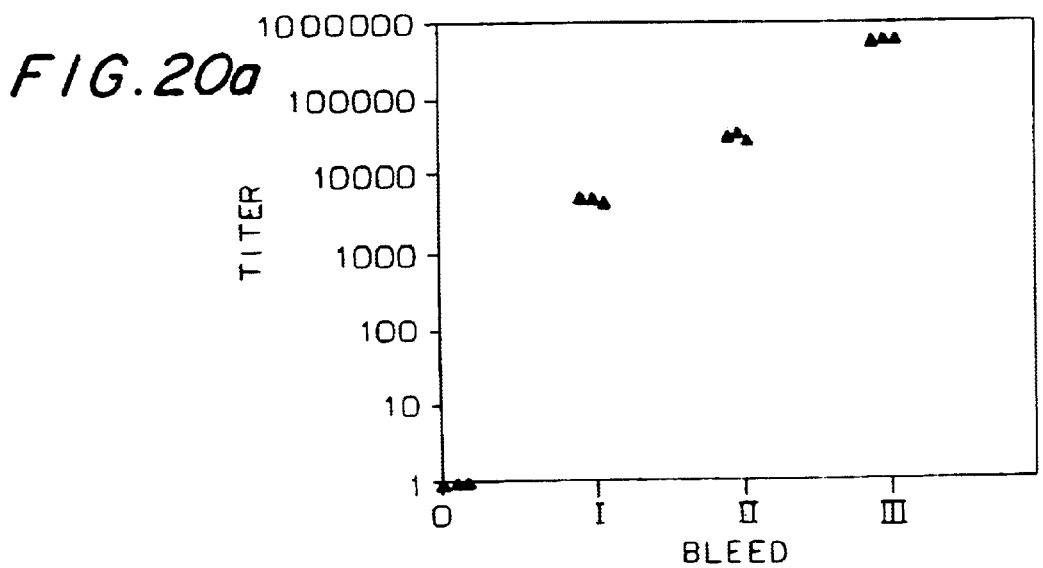
FIGS. 20*a* and 20*b* show immunization with f3 filamentous phage displaying EFRH (SEQ ID NO:1) epitope of β-amhyloid peptide as a fusion of phage glycoprotein III (gpIII). Serum IgG titer of different bleeds from mice immunized with the EFRH-phage according to the schedule of FIG. 19 against wild type filamentous phage coat proteins (FIG. 20a) and the N-terminal epitope (acids 1–16, SEQ ID NO:3) of β-amyloid (FIG. 20b).
Figure 20B:
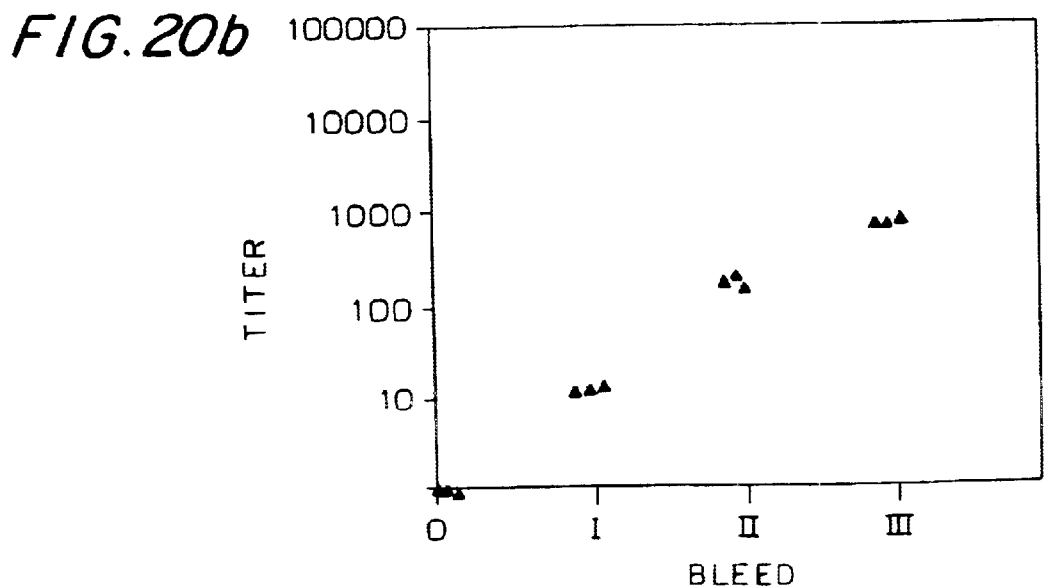
Figure 21:
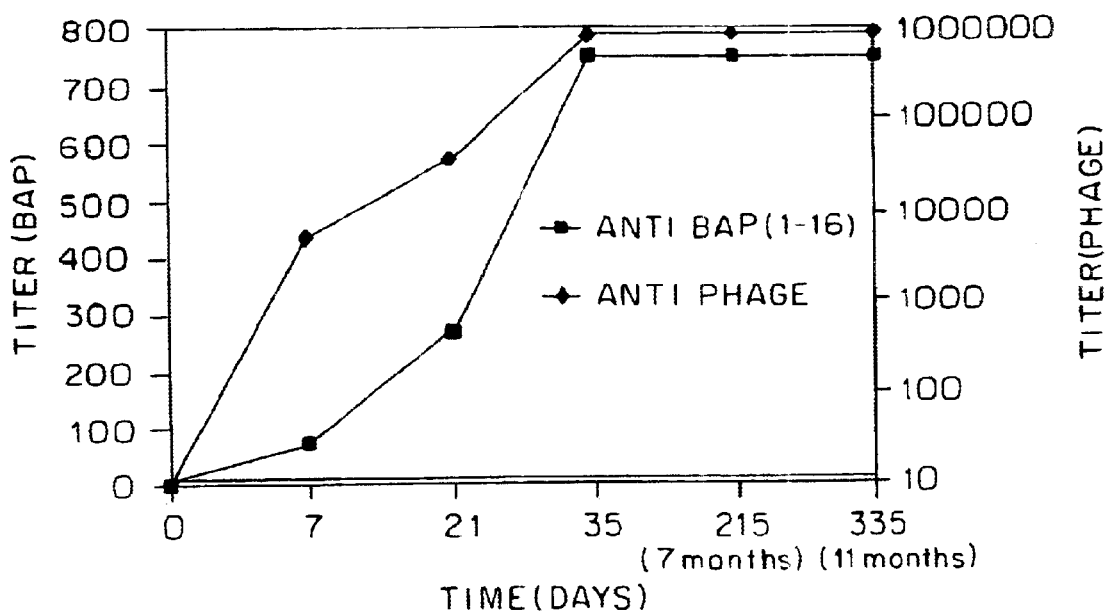
FIG. 21 demonstrates long lasting immunization with f3 filamentous phage. Serum IgG titer of different bleeds from mice immunized with EFRH-phage against wild type filamentous phage coat proteins and the N-terminal (acids 1–16, SEQ ID NO:3) of β-amhyloid.

Raising Anti-aggregating βAP Antibody through Immunization of Mice with f3-EFRH Phage The anti-aggregating epitope within βAP (EFRH, SEQ ID NO:1) map to positions 3–6 of the amino acid sequence of βAP. In order to generate specific immune response against βAP, mice were immunized with genetically engineered fd phage carrying the peptide YYEFRH (SEQ ID NO:7) fused to its minor coat gpIII according to the immunization schedule shown in FIG. 19. Doses of $10^{10}$ phage particles per injection were used to immunize, at 14-day intervals, through intraperitoneal injection. Following 7 days of each injection, mice were bled and their sera tested by ELISA for IgG antibody reactivity against wild type phage (not bearing the peptide YYEFRH on its surface) and against βAP (FIGS. 20a–b). This route of administration a very high response against βAP (1:750) following the third injection. Furthermore, it was found that injection through phage carrying epitope is long lasting (FIG. 21), it is none toxic and may be given without adjuvant. The phage vector is found to be an immunogenic tool to raise a high affinity immune response within 14 days from the first injection. The immune response against the peptide YYEFRH (SEQ ID NO:7) is low compared to the immune response against the entire phage and could be explained by the low copy number of the fusion gpIII on the phage envelope. Therefore, for further analysis phages displaying the epitope through glycoprotein VIII were employed.

Example 10

Isolation of f88-EFRH Peptide-displayed Phage by an Anti-aggregating mAb

To identify a disagreggating EFRH peptide epitope a phage-epitope library was screened with biotinylated antibody. After three cycles of panning and phage amplification, 90 individually isolated bacterial colonies were grown in microtiter plates and their phages were assayed for antibody binding. ELISA analysis revealed that of the phage-clones which were selected followed by three biopanning cycles, most (above 80%) bound specifically to anti-aggregating mAb, respectively. DNA from 6 positive clones was sequenced (Table 2). The sequence EFRH (SEQ ID NO:1) appeared in 4 clones, one additional clone had the sequence EPRH (SEQ ID NO:1), with only one residue replacement of proline with phenylalanine. In one additional clone, the inserted peptide bears the sequence of the three residues FRH (acids 2–4 of SEQ ID NO:1), lacking the glutamate residue.

TABLE 2

| Amino acid Sequence (name) | SEQ ID NO: | No. of phages |
|---|---|---|
| VHEPHEFRHVALNPV (C3-II) | 8 | 2 |
| DTEFRHSSNNFSAVR (C7-II) | 21 | 1 |
| STEFRHQTTPLHPNS (C11-I) | 22 | 1 |
| KEPRHHIQHHERVIR (F8-II) | 23 | 1 |
| SAADFRHGSPPISAF (D3-I) | 24 | 1 |

Figure 22:
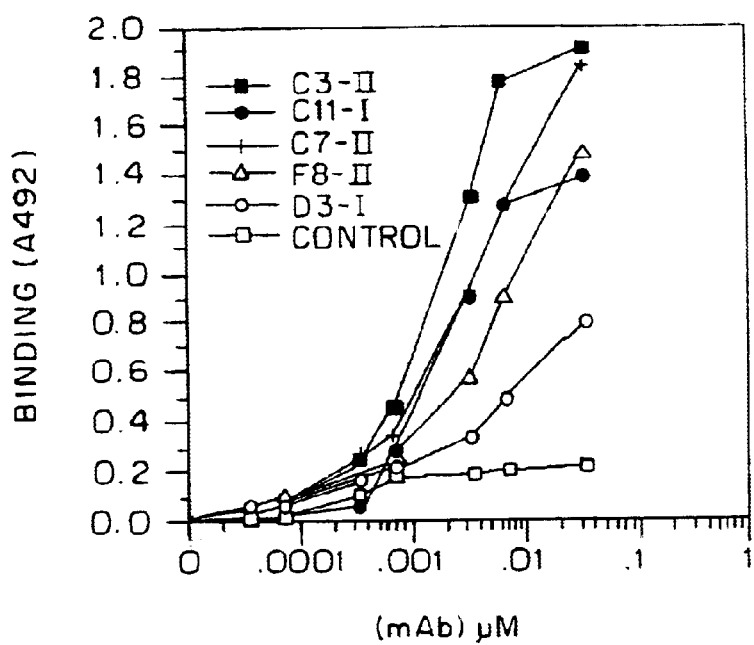
FIG. 22 show binding of anti-aggregating βAP monoclonal antibody (mAb 10D5) to peptide-presenting phage selected from an f88 phage library. Unrelated mAb 5.5 raised against acetylcholine receptor was used as a negative control. Antibodies were added to phage-coated wells and ELISA was used to detect binding.
Figure 23:
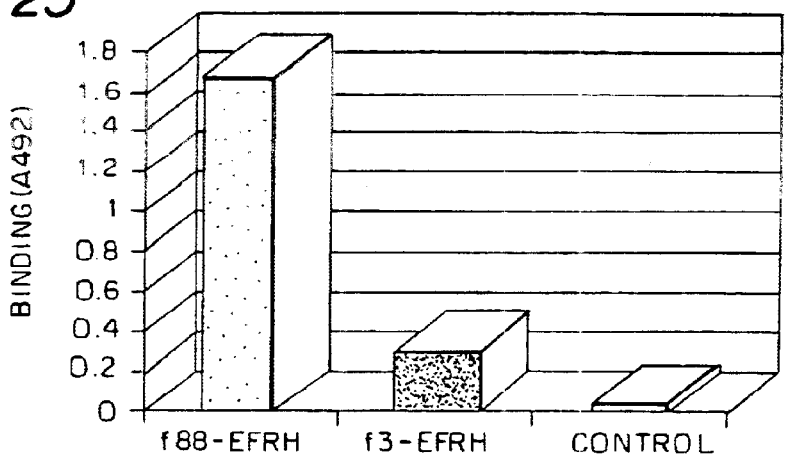
FIG. 23 show binding of anti-aggregating βAP mAb (10D5) to a YYEFRH (SEQ ID NO:7)-phage and VHEPHEFRHVALNPV (SEQ ID NO:8)-phage. Antibody in concentration of 1 μg/ml was added to phage-coated wells and binding was analyzed by ELISA. Filamentous phage without insert was used as a control.

Binding of anti-aggregating mAb to the EFRH-bearing phage was concentration dependent; half-maximal binding was obtained at an antibody concentration of 100 ng/ml, corresponding to $10^{-9}$ M (FIG. 4) which resembles the level of binding of these antibodies to the whole peptide. One specific f88-EFRH phage (termed C3-II, table 2) showed higher level of avidity as is compared to the others (FIG. 22). It may be due to higher level of EFRH epitope exposure on its surface. Binding tests of f88-EFRH or f3-EFRH with the same concentration of anti-aggregating antibody (1μ/ml) demonstrated a higher number of EFRH epitope copies per phage which may lead to higher serum titer via phage immune response (FIG. 23).

Example 11

Figure 24A:
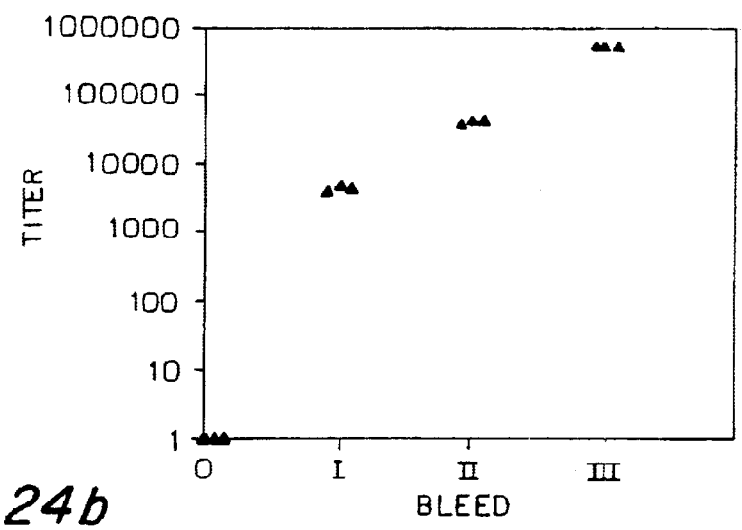
FIGS. 24(a–b) show immunization with f88 filamentous phage displaying EFRH (SEQ ID NO: 1) epitope of β-amhyloid peptide as a fusion of phage glycoprotein VIII (gpVIII). Serum IgG titer of different bleeds from mice immunized with EFRH-phage against wild type filamentous phage coat proteins (FIG. 24a) and the N-terminal epitope (acids 1–16, SEQ ID NO:3) of β-amyloid peptide (FIG. 24b).
Figure 24B:
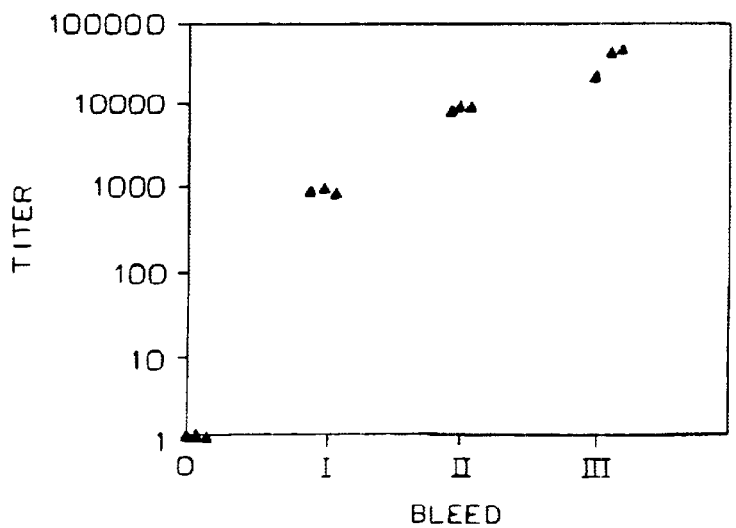

Raising Anti-aggregating βAP Antibody through Immunization of Mice with f88-phage In order to generate the same specific immune response against β AP, mice were immunized with genetically engineered fd phage carrying the peptide VHEPH EFRHVALNPV (SEQ ID NO:8) fused to its major coat gpVIII. This phage was selected from a 15-mer phage peptide library by an anti aggregating βAP antibody and is presenting the mAb epitope (underlined) within βAP. This phage was used to immunize mice as described. Following 7 days of each injection with $10^{10}$ phage particles (without adjuvant) the mice were bled and their sera tested by ELISA for IgG antibody reactivity against wild type phage and against βAP. The results are summarized in FIGS. 24a–b. All animals showed a measurable response of IgG antibody against the wild type phage, and titers increased with the second and the third injection. This route also gave the highest titer measurable responses against βAP (1:50,000) after the third injection (FIG. 24b).

Example 12

Inhibition of Antibody Serum Binding to β-amyloid Peptide

Figure 25:
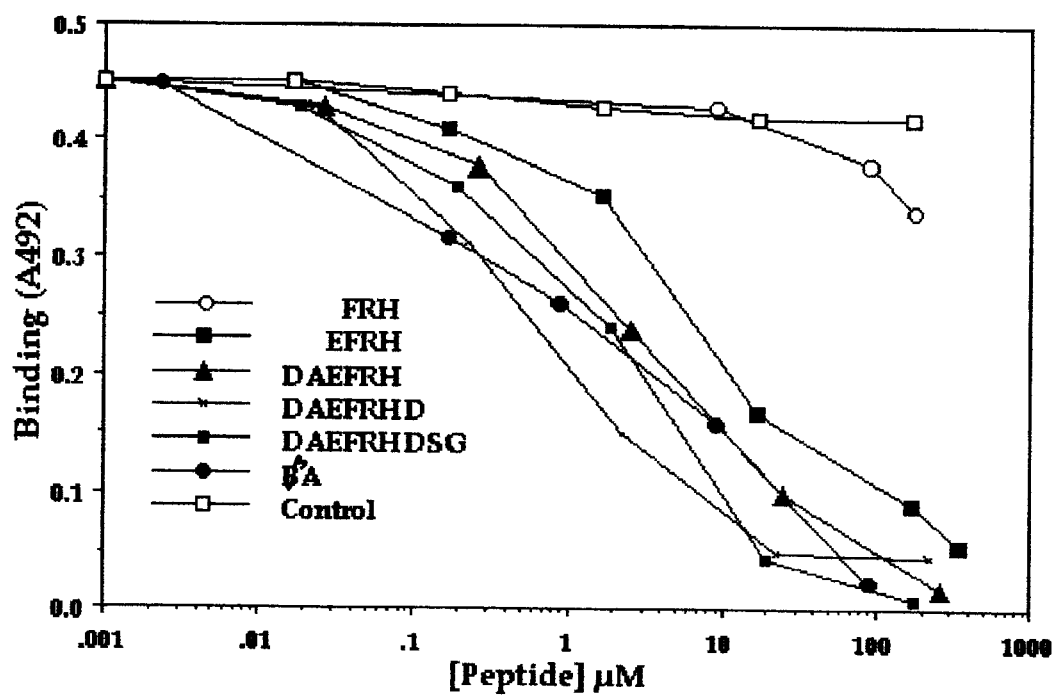
FIG. 25 shows inhibition of serum of an immunized mice in binding to βAP by synthetic peptides derived from the N-terminal of β-amyloid peptide. The assay was done with 1:3000 dilution of serum after a third immunization with f88-EFRH reacted with the various peptides in various concentrations per well, as indicated. The peptide WVLD (SEQ ID NO:4) was used as a negative control.

The interaction of mouse serum immunized by phage f88-EFRH with βAP was further assayed by competitive inhibition experiments. FIG. 25 shows inhibition of mice serum antibody with synthesized peptides derived from βAP, each of which includes the sequence EFRH) such as: DAEFRH (positions 1–6, SEQ ID NO:3), DAEFRHD (positions 1–7, SEQ ID NO:3), DAEFRHDSG (positions 1–9, SEQ ID NO:3), and βAP itself, DAEFRHDSGYEV$_{H}$-HQKLVFFAEDVGSNKGAIIGLMVGGVV (positions 1–40, SEQ ID NO:3).

FIG. 25 shows that all of the synthetic peptides which bear the motive EFRH (SEQ ID NO:1) similarly inhibited binding of mouse serum antibody to the βAP with $IC_{50}$ values of about $5 \times 10^{-6}$ M. These data indicate that the epitope of mouse serum antibody within the βAP molecule is composed of four amino acid residues corresponding to positions 3–6 in the βAP which was found to act as a regulatory site controlling both the solubilization and the disaggregation process of the βA molecule.

Example 13

Figure 26:
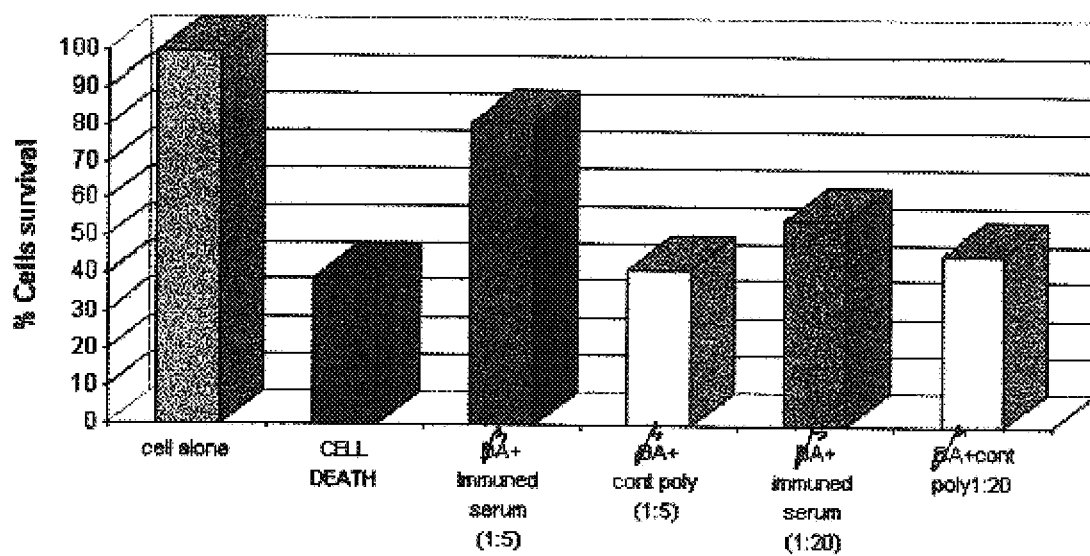
FIG. 26 demonstrates prevention of βAP mediated toxic effect on PC12 cells by serum antibodies raised against f88-EFRH-phage. Cells were incubated with fibrillar βA alone, or with fibrillar βA that has been incubated with serum from the third bleeding at different concentration. The negative control was serum from a non-immunized mouse. The MTT assay was used to estimate cell survival.

Prevention of the βamyloid Neurotoxic Effect by Serum Antibody Raised Against EFRH-phage In order to find out whether serum of f88-EFRH immunized mice exhibits a protective effect similar to the parental IgG antibody in preventing βA mediated neurotoxicity toward cultured cells, the in vitro test using rat phenochromocytoma PC12 was applied as described (Solomon B. et al., Proc. Natl. Acad. Sci. USA., 94: 4109–4112,1997). Viability of the cells exposed to βA with or without antibody was measured. As shown in FIG. 26, diluted serum of 1:5 prevented the neurotoxicity of βA (80% cell viability), while the unrelated serum showed no effect.

Example 14

Disaggregation of β-amyloid Fibril by Serum of EFRH Immunized Mice

Figure 27:
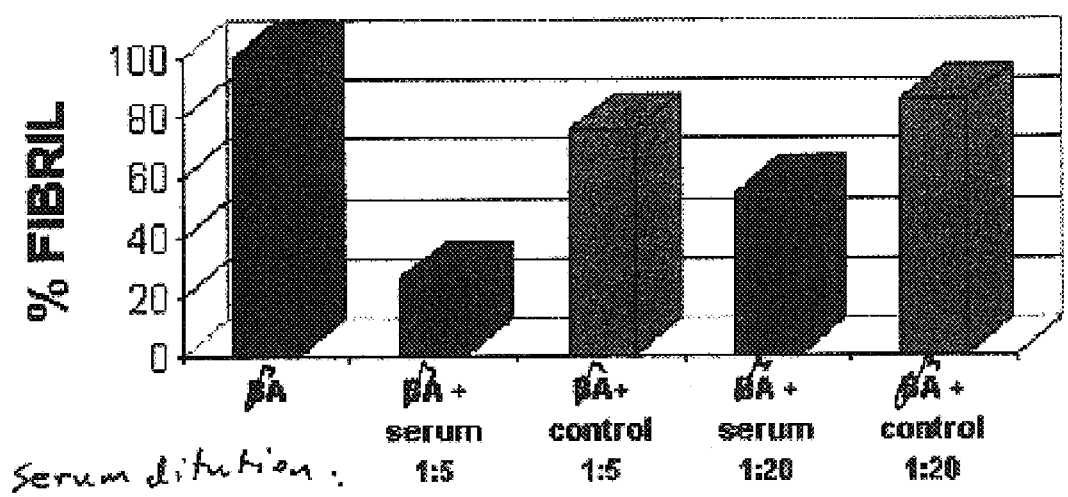
FIG. 27 demonstrates interference with fibrillar β-amhyloid formation by serum antibodies raised against the f88-EFRH-phage. Estimation of the fluorescence of ThT which correlates with the amount of fibrillar β-amhyloid formed after incubation for a week at 37° C. in the presence of serum samples diluted as indicated. The negative control was serum from a non-immunized mouse. The positive control was without serum. Fibril formation was measured by the ThT assay.

To examine the effect of serum of f88-EFRH immunized mice on disruption of the βA fibril (the toxic form of βAP) the ThT reagent that binds specifically to fibrillar structures (Levine, H. III, Protein Sci., 2: 404–410,1993) was used. βAP samples were incubated for a week at 37° C. and then were exposed to different dilutions mouse serum antibody. Fibril formation was quantitated by the ThT fluorometry binding assay. FIG. 27 shows that mouse serum, at dilution of 1:5 and 1:20, disrupted the fibril structure of βA with extensive deterioration of fibril morphology, as indicated by a substantial 75% (1:5 dilution) and 50% (1:20 dilution) decrease in ThT fluorescence. The unrelated serum used as control (serum from non-immunized mouse), did not significantly inhibit fibril formation as is compared to the immunized serum. This result strongly emphasizes the ability of the EFRH epitope displayed by a filamentous phage vector to evoke an immune response resulting in anti-agreggation antibody.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications cited herein are incorporated by reference in their entirety.

What is claimed is:

1. A pharmaceutical composition in unit dosage form, comprising a pharmaceutically acceptable carrier and, as active ingredient, a filamentous bacteriophage displaying an epitope of beta-amyloid, so as to elicit antibodies against said epitope when administered to a subject, wherein said antibodies inhibit aggregation of said beta-amyloid in the subject and/or cause disaggregation of any beta-amyloid aggregate in the subject.

2. The pharmaceutical composition of claim 1, wherein said bacteriophage propagates in bacterial flora of a recipient.

3. The pharmaceutical composition of claim 1, wherein said bacteriophage propagates in *Escherichia coli*.

4. The pharmaceutical composition of claim 1, wherein said bacteriophage is fd.

5. The pharmaceutical composition of claim 1, wherein said active ingredient is selected such that less than 30 days following an introduction of a triple dose of $10^{10}$ units thereof to a recipient, a titer of said antibodies is above 1:50,000, as is determined by ELISA.

6. A pharmaceutical composition in accordance with claim 1, wherein said epitope of beta-amyloid is disolayed via coat glycoprotein VIII on said bacteriophage.

7. The pharmaceutical composition of claim 1, wherein said bacteriophage is M13.

8. A pharmaceutical composition in accordance with claim 1, wherein said filamentous bacteriophage displays SEQ ID NO:1.

9. A pharmaceutical composition in accordance with claim 1, wherein said filamentous bacteriophage displays a peptide selected from the group consisting of SEQ ID NO:3, SEQ ID NO:7, SEQ ID NO:8, SEQ ID NO:21, and SEQ ID NO:22.

10. A pharmaceutical composition in accordance with claim 9, wherein said epitope of beta-amyloid is displayed via coat glycoprotein VIII on said bacteriophage.

11. A pharmaceutical composition in accordance with claim 9, wherein said epitope of beta-amyloid is displayed via coat glycoprotein VIII on said bacteriophage.

* * * * *

UNITED STATES PATENT AND TRADEMARK OFFICE
CERTIFICATE OF CORRECTION

PATENT NO. : 6,703,015 B1
DATED : March 9, 2004
INVENTOR(S) : Beka Solomon and Dan Frenkel It is certified that error appears in the above-identified patent and that said Letters Patent is hereby corrected as shown below:

Title page, Item [54] and Column 1, line 2,
Title, delete "AN" and insert therefor -- A --

Title page,
Item [56], References Cited, OTHER PUBLICATIONS, "J.K. Scott et al.," reference, delete "brai AB burden in alzheimer's" and insert therefor -- brain AB burden in Alzheimer's --
"Dave Morgan" reference, delete "prvents memory loss inan" and insert therefor -- prevents memoray loss in an --
"Christopher Janus" reference, delete "modelof alzhe-" and insert therefor -- model of Alzhei- --
"Anne E. Willis et al.," reference, delete "ona" and insert therefor -- on a --
"Cesareni et al.," reference, delete "Minireview Peptides" and insert therefor -- Peptide -- delete "capsids a" and insert therefor -- capsids. A --
"Wetzel," reference, delete "Commentary learning" and insert therefor -- Learning --
"Clackson et al.," reference, delete "Letters to nature making" and insert therefor -- Making --
"McCafferty et al.," reference, delete "Letters to nature phage" and insert therefor -- Phage --
"Schenk et al.," reference, delete "Letters to nature immunization" and insert therefor -- Immunization --
"Solomon et al.," reference, delete "mAB" and insert -- mAb -- after "4109-4112", insert -- (1997) --
Item [57], ABSTRACT,
Line 11, delete "desegregation" and insert therefor -- disaggregation --

Column 1,
Line 16, delete "formnation" and insert therefor -- formation --

Column 2,
Line 38, after "more", delete "." and insert therefor -- , --

Column 4,
Line 13, delete "displayvehicle" and insert therefor -- display vehicle --

Column 8,
Line 22, delete "is"
Line 36, delete "hipocampous" and insert therefor -- hippocampus --
Line 50, delete "as is compare" and insert therefor -- is compared --
Lines 64 and 67, delete "$\beta$ -amhyloid" and insert therefor -- $\beta$-amyloid --

UNITED STATES PATENT AND TRADEMARK OFFICE
CERTIFICATE OF CORRECTION

PATENT NO. : 6,703,015 B1
DATED : March 9, 2004
INVENTOR(S) : Beka Solomon and Dan Frenkel It is certified that error appears in the above-identified patent and that said Letters Patent is hereby corrected as shown below:

Column 9,
Lines 25, 47 and 49, delete "β-amhyloid" and insert therefor -- β-amyloid --

Column 11,
Line 29, after "present" insert -- invention --
Line 66, delete "a" and insert therefor -- the resulting --
Line 66, after "titers", insert -- . --

Column 12,
Line 1, delete "which result."
Line 12, delete "AP" and insert therefor -- βAP --

Column 13,
Line 26, delete "β-amhyloid" and insert therefor -- β-amyloid --

Column 16,
Line 16, delete "InAbs" and insert therefor -- mAbs --
Line 43, after "only" insert -- to --

Column 16,
Line 39, delete "iunctionalities" and insert therefor -- functionalities --

Column 18,
Line 21, delete "β-amhyloid" and insert therefor -- β-amyloid --

Column 20,
Line 2, delete "inrtaperitoneal" and insert therefor -- intraperitoneal --

Column 24,
Line 38, delete "1o"

Column 25,
Line 37, delete "Fiamyloid" and insert therefor -- β-amyloid --

Column 26,
Lines 32 and 34, delete "β-amhyloid" and insert therefor -- β-amyloid --
Line 60, delete "carries by a fillamentous" and insert therefor -- carried by a filamentous --

UNITED STATES PATENT AND TRADEMARK OFFICE
CERTIFICATE OF CORRECTION

PATENT NO. : 6,703,015 B1
DATED : March 9, 2004
INVENTOR(S) : Beka Solomon and Dan Frenkel It is certified that error appears in the above-identified patent and that said Letters Patent is hereby corrected as shown below:

Column 27,
Lines 15 and 23, delete "thick-nesses" and insert therefor -- thicknesses --
Line 52, after "injected", insert -- with --

Column 29,
Line 18, delete "β-amyloidpeptide" and insert therefor -- β-amyloid peptide --
Line 34, delete "synthesis" and insert therefor -- synthesized --
Line 46, delete "β-amhyloid" and insert therefor -- β-amyloid --

Column 30,
Line 8, delete "beta-amnyloid" and insert therefor -- beta-amyloid --
Lines 26 and 37, delete "β-amhyloid" and insert therefor -- β-amyloid --

Column 32,
Line 57, delete "propose" and insert therefor -- purpose --
Lines 59 and 64, delete "hipocampous" and insert therefor -- hippocampus --

Column 33,
Lines 3 and 6, delete "hypocampous" and insert therefor -- hippocampus --
Line 11, delete "are" and insert therefor -- Is --
Line 49, after "administration", insert -- gave --
Line 52, delete "none toxic" and insert therefor -- non-toxic --

Column 34,
Line 10, delete " (SEQ ID NO:1)" and insert therefor -- (residues 2-5 of SEQ ID NO: 23) --

Column 35,
Line 20, delete "βamyloid" and insert therefor -- β-amyloid --

UNITED STATES PATENT AND TRADEMARK OFFICE
CERTIFICATE OF CORRECTION

PATENT NO. : 6,703,015 B1
DATED : March 9, 2004
INVENTOR(S) : Beka Solomon and Dan Frenkel It is certified that error appears in the above-identified patent and that said Letters Patent is hereby corrected as shown below:

Column 36,
Line 11, after "dilutions", insert -- of --

Signed and Sealed this

Fifth Day of July, 2005

JON W. DUDAS
*Director of the United States Patent and Trademark Office*

SEQUENCE LISTING

```
<160> NUMBER OF SEQ ID NOS: 26

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Glu Phe Arg His
1

<210> SEQ ID NO 2
<211> LENGTH: 15
<212> TYPE: PRT
<213> ORGANISM: Artificial Sequence
<220> FEATURE:
<223> OTHER INFORMATION: synthetic peptide

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 43
<212> TYPE: PRT
<213> ORGANISM: Artificial Sequence
<220> FEATURE:
<223> OTHER INFORMATION: synthetic peptide
```

-continued

```
<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

<210> SEQ ID NO 4
<211> LENGTH: 4
<212> TYPE: PRT
<213> ORGANISM: Artificial Sequence
<220> FEATURE:
<223> OTHER INFORMATION: synthetic peptide

<400> SEQUENCE: 4

Trp Val Leu Asp
1

<210> SEQ ID NO 5
<211> LENGTH: 717
<212> TYPE: DNA
<213> ORGANISM: Homo sapiens
<220> FEATURE:
<221> NAME/KEY: CDS
<222> LOCATION: (1)..(717)

<400> SEQUENCE: 5 cag gtc aaa ctg cag gag tca ggg gct gag ctg gtg agg cct ggg gtc      48
Gln Val Lys Leu Gln Glu Ser Gly Ala Glu Leu Val Arg Pro Gly Val
1               5                   10                  15 tca gtg aag att tcc tgc aag ggt tct ggc tac aca ttc act gat tat      96
Ser Val Lys Ile Ser Cys Lys Gly Ser Gly Tyr Thr Phe Thr Asp Tyr
            20                  25                  30 gct atg cac tgg gtg aag cag agt cat gca aag agt cta gag tgg att     144
Ala Met His Trp Val Lys Gln Ser His Ala Lys Ser Leu Glu Trp Ile
        35                  40                  45 gga gtt att agt act tac tat ggt gat gct agc tac aac cag aag ttc     192
Gly Val Ile Ser Thr Tyr Tyr Gly Asp Ala Ser Tyr Asn Gln Lys Phe
    50                  55                  60 aag ggc aag gcc aca atg act gta gac aaa tcc tcc agc aca gcc tat     240
Lys Gly Lys Ala Thr Met Thr Val Asp Lys Ser Ser Ser Thr Ala Tyr
65                  70                  75                  80 atg gaa ctt gcc aga ctg aca tct gag gat tct gcc atc tat tac tgt     288
Met Glu Leu Ala Arg Leu Thr Ser Glu Asp Ser Ala Ile Tyr Tyr Cys
                85                  90                  95 gca aga ggg gct act atg tcc tac ttt gac tac tgg ggc caa gtg acc     336
Ala Arg Gly Ala Thr Met Ser Tyr Phe Asp Tyr Trp Gly Gln Val Thr
            100                 105                 110 acg gtc acc gtc tcc tca ggt gga ggc ggt tca ggc gga gtt ggc tct     384
Thr Val Thr Val Ser Ser Gly Gly Gly Gly Ser Gly Gly Val Gly Ser
        115                 120                 125 ggc ggt ggc gga tcg gac atc gag ctc act cag tct cca gca atc atg     432
Gly Gly Gly Gly Ser Asp Ile Glu Leu Thr Gln Ser Pro Ala Ile Met
    130                 135                 140 tct gca tct cca ggg gag aag gtc acc atg acc tgc agt gcc agc tca     480
Ser Ala Ser Pro Gly Glu Lys Val Thr Met Thr Cys Ser Ala Ser Ser
145                 150                 155                 160 agt ata agt tac atg cac tgg tat cag cag aag cca ggc acc tcc ccc     528
Ser Ile Ser Tyr Met His Trp Tyr Gln Gln Lys Pro Gly Thr Ser Pro
                165                 170                 175
```

```
aaa aga tgg att tat gac aca tcc aaa ctg gct tct gga gtc cct gct    576
Lys Arg Trp Ile Tyr Asp Thr Ser Lys Leu Ala Ser Gly Val Pro Ala
        180                 185                 190 cgc ttc agt ggc agt ggg tct ggg acc tct tat tct ctc aca atc agc    624
Arg Phe Ser Gly Ser Gly Ser Gly Thr Ser Tyr Ser Leu Thr Ile Ser
    195                 200                 205 agc atg gag gct gaa gat gct gcc act tat tac tgc cat cag cgg agt    672
Ser Met Glu Ala Glu Asp Ala Ala Thr Tyr Tyr Cys His Gln Arg Ser
    210                 215                 220 agt tac cca ttc acg ttc gga ggg ggg gcc aag ctg gaa ata aaa        717
Ser Tyr Pro Phe Thr Phe Gly Gly Gly Ala Lys Leu Glu Ile Lys
225                 230                 235
```

<210> SEQ ID NO 6
<211> LENGTH: 239
<212> TYPE: PRT
<213> ORGANISM: Homo sapiens

<400> SEQUENCE: 6

```
Gln Val Lys Leu Gln Glu Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Val Ile Ser Thr Tyr Tyr Gly Asp Ala Ser Tyr Asn Gln Lys Phe
    50                  55                  60

Lys Gly Lys Ala Thr Met Thr Val Asp Lys Ser Ser Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Ala Thr Met Ser Tyr Phe Asp Tyr Trp Gly Gln Val Thr
            100                 105                 110

Thr Val Thr Val Ser Ser Gly Gly Gly Gly Ser Gly Gly Val Gly Ser
        115                 120                 125

Gly Gly Gly Gly Ser Asp Ile Glu Leu Thr Gln Ser Pro Ala Ile Met
    130                 135                 140

Ser Ala Ser Pro Gly Glu Lys Val Thr Met Thr Cys Ser Ala Ser Ser
145                 150                 155                 160

Ser Ile Ser Tyr Met His Trp Tyr Gln Gln Lys Pro Gly Thr Ser Pro
                165                 170                 175

Lys Arg Trp Ile Tyr Asp Thr Ser Lys Leu Ala Ser Gly Val Pro Ala
            180                 185                 190

Arg Phe Ser Gly Ser Gly Ser Gly Thr Ser Tyr Ser Leu Thr Ile Ser
        195                 200                 205

Ser Met Glu Ala Glu Asp Ala Ala Thr Tyr Tyr Cys His Gln Arg Ser
    210                 215                 220

Ser Tyr Pro Phe Thr Phe Gly Gly Gly Ala Lys Leu Glu Ile Lys
225                 230                 235
```

<210> SEQ ID NO 7
<211> LENGTH: 6
<212> TYPE: PRT
<213> ORGANISM: Artificial Sequence
<220> FEATURE:
<223> OTHER INFORMATION: synthetic peptide

<400> SEQUENCE: 7

Tyr Tyr Glu Phe Arg His
1               5

<210> SEQ ID NO 8
<211> LENGTH: 15
<212> TYPE: PRT
<213> ORGANISM: Artificial Sequence
<220> FEATURE:
<223> OTHER INFORMATION: synthetic peptide

<400> SEQUENCE: 8

Val His Glu Pro His Glu Phe Arg His Val Ala Leu Asn Pro Val
1               5                   10                  15

<210> SEQ ID NO 9
<211> LENGTH: 3
<212> TYPE: PRT
<213> ORGANISM: Artificial Sequence
<220> FEATURE:
<223> OTHER INFORMATION: synthetic peptide

<400> SEQUENCE: 9

Lys Leu His
1

<210> SEQ ID NO 10
<211> LENGTH: 45
<212> TYPE: DNA
<213> ORGANISM: Artificial Sequence
<220> FEATURE:
<223> OTHER INFORMATION: primer
<221> NAME/KEY: misc_feature
<223> OTHER INFORMATION: "n" at position 17 is unknown

<400> SEQUENCE: 10
cccccctccg aacgtsnatg ggtaactcga tcgctgatgg cagta          45

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
atctatgcgg cccagccggc catg                                 24

<210> SEQ ID NO 12
<211> LENGTH: 38
<212> TYPE: DNA
<213> ORGANISM: Artificial Sequence
<220> FEATURE:
<223> OTHER INFORMATION: primer

<400> SEQUENCE: 12
gtggtgctga gtggatccta tactacactg ccaccggg                  38

<210> SEQ ID NO 13
<211> LENGTH: 58
<212> TYPE: DNA
<213> ORGANISM: Artificial Sequence
<220> FEATURE:
<223> OTHER INFORMATION: primer

<400> SEQUENCE: 13
agctccgatg ctgaattcgg tgatagcggc tacgaagtgc atcatcagaa acctgcag   58

<210> SEQ ID NO 14
<211> LENGTH: 52
<212> TYPE: DNA
<213> ORGANISM: Artificial Sequence
<220> FEATURE:
<223> OTHER INFORMATION: primer

<400> SEQUENCE: 14
ggtttctgat gatgcacttc gtagccgcta tcatgacgaa attcagcatc gg        52

<210> SEQ ID NO 15
<211> LENGTH: 9
<212> TYPE: PRT
<213> ORGANISM: Artificial Sequence
<220> FEATURE:
<223> OTHER INFORMATION: synthetic peptide

<400> SEQUENCE: 15

His Gln Arg Ser Ser Tyr Pro Cys Thr
1               5

<210> SEQ ID NO 16
<211> LENGTH: 9
<212> TYPE: PRT
<213> ORGANISM: Artificial Sequence
<220> FEATURE:
<223> OTHER INFORMATION: synthetic peptide

<400> SEQUENCE: 16

His Gln Arg Ser Ser Tyr Pro Cys Thr
1               5

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

His Gln Arg Ser Ser Tyr Pro Phe Thr
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic peptide

<400> SEQUENCE: 18

His Gln Arg Ser Ser Tyr Pro Tyr Thr
1               5

<210> SEQ ID NO 19
<211> LENGTH: 9
<212> TYPE: PRT
<213> ORGANISM: Artificial Sequence
<220> FEATURE:
<223> OTHER INFORMATION: synthetic peptide

<400> SEQUENCE: 19

His Gln Arg Ser Ser Tyr Pro Phe Thr
1               5

<210> SEQ ID NO 20

<211> LENGTH: 9
<212> TYPE: PRT
<213> ORGANISM: Artificial Sequence
<220> FEATURE:
<223> OTHER INFORMATION: synthetic peptide

<400> SEQUENCE: 20

His Gln Arg Ser Ser Tyr Pro Ser Thr
1               5

<210> SEQ ID NO 21
<211> LENGTH: 15
<212> TYPE: PRT
<213> ORGANISM: Artificial Sequence
<220> FEATURE:
<223> OTHER INFORMATION: synthetic peptide

<400> SEQUENCE: 21

Asp Thr Glu Phe Arg His Ser Ser Asn Asn Phe Ser Ala Val Arg
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: synthetic peptide

<400> SEQUENCE: 22

Ser Thr Glu Phe Arg His Gln Thr Thr Pro Leu His Pro Asn Ser
1               5                   10                  15

<210> SEQ ID NO 23
<211> LENGTH: 15
<212> TYPE: PRT
<213> ORGANISM: Artificial Sequence
<220> FEATURE:
<223> OTHER INFORMATION: synthetic peptide

<400> SEQUENCE: 23

Lys Glu Pro Arg His His Ile Gln His His Glu Arg Val Ile Arg
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: synthetic peptide

<400> SEQUENCE: 24

Ser Ala Ala Asp Phe Arg His Gly Ser Pro Pro Ile Ser Ala Phe
1               5                   10                  15

<210> SEQ ID NO 25
<211> LENGTH: 357
<212> TYPE: DNA
<213> ORGANISM: synthetic construct
<220> FEATURE:
<221> NAME/KEY: CDS
<222> LOCATION: (1)..(357)

<400> SEQUENCE: 25 ggc ggt tca ggc gga gtt ggc tct ggc ggt ggc gga tcg gac atc gag     48
Gly Gly Ser Gly Gly Val Gly Ser Gly Gly Gly Gly Ser Asp Ile Glu
1               5                   10                  15 ctc act cag tct cca gca atc atg tct gca tct cca ggg gag aag gtc     96

```
                                     -continued

Leu Thr Gln Ser Pro Ala Ile Met Ser Ala Ser Pro Gly Glu Lys Val
        20                  25                  30 acc atg acc tgc agt gcc agc tca agt ata agt tac atg cac tgg tat      144
Thr Met Thr Cys Ser Ala Ser Ser Ser Ile Ser Tyr Met His Trp Tyr
        35                  40                  45 cag cag aag cca ggc acc tcc ccc aaa aga tgg att tat gac aca tcc      192
Gln Gln Lys Pro Gly Thr Ser Pro Lys Arg Trp Ile Tyr Asp Thr Ser
 50                  55                  60 aaa ctg gct tct gga gtc cct gct cgc ttc agt ggc agt ggg tct ggg      240
Lys Leu Ala Ser Gly Val Pro Ala Arg Phe Ser Gly Ser Gly Ser Gly
 65                  70                  75                  80 acc tct tat tct ctc aca atc agc agc atg gag gct gaa gat gct gcc      288
Thr Ser Tyr Ser Leu Thr Ile Ser Ser Met Glu Ala Glu Asp Ala Ala
                85                  90                  95 act tat tac tgc cat cag cgg agt agt tac cca ttc acg ttc gga ggg      336
Thr Tyr Tyr Cys His Gln Arg Ser Ser Tyr Pro Phe Thr Phe Gly Gly
            100                 105                 110 ggg gcc aag ctg gaa ata aaa                                          357
Gly Ala Lys Leu Glu Ile Lys
        115

<210> SEQ ID NO 26
<211> LENGTH: 119
<212> TYPE: PRT
<213> ORGANISM: synthetic construct

<400> SEQUENCE: 26

Gly Gly Ser Gly Gly Val Gly Ser Gly Gly Gly Ser Asp Ile Glu
 1               5                  10                  15

Leu Thr Gln Ser Pro Ala Ile Met Ser Ala Ser Pro Gly Glu Lys Val
        20                  25                  30

Thr Met Thr Cys Ser Ala Ser Ser Ser Ile Ser Tyr Met His Trp Tyr
        35                  40                  45

Gln Gln Lys Pro Gly Thr Ser Pro Lys Arg Trp Ile Tyr Asp Thr Ser
 50                  55                  60

Lys Leu Ala Ser Gly Val Pro Ala Arg Phe Ser Gly Ser Gly Ser Gly
 65                  70                  75                  80

Thr Ser Tyr Ser Leu Thr Ile Ser Ser Met Glu Ala Glu Asp Ala Ala
                85                  90                  95

Thr Tyr Tyr Cys His Gln Arg Ser Ser Tyr Pro Phe Thr Phe Gly Gly
            100                 105                 110

Gly Ala Lys Leu Glu Ile Lys
        115
```